US009845513B2

(12) United States Patent
Dole et al.

(10) Patent No.: US 9,845,513 B2
(45) Date of Patent: Dec. 19, 2017

(54) METHOD OF PRODUCING SUCCINIC ACID AND OTHER CHEMICALS USING SUCROSE-CONTAINING FEEDSTOCK

(75) Inventors: Sudhandshu Dole, North Andover, MA (US); R. Rogers Yocum, Lexington, MA (US); Theron Hermann, Arlington, MA (US); Xiaohui Yu, Woburn, MA (US)

(73) Assignee: Myriant Corporation, Woburn, MA (US)

( * ) Notice: Subject to any disclaimer, the term of this patent is extended or adjusted under 35 U.S.C. 154(b) by 0 days.

(21) Appl. No.: 13/993,150

(22) PCT Filed: Dec. 13, 2011

(86) PCT No.: PCT/US2011/064598
§ 371 (c)(1),
(2), (4) Date: Aug. 26, 2013

(87) PCT Pub. No.: WO2012/082720
PCT Pub. Date: Jun. 21, 2012

(65) Prior Publication Data
US 2013/0337519 A1    Dec. 19, 2013

Related U.S. Application Data

(60) Provisional application No. 61/459,446, filed on Dec. 13, 2010.

(51) Int. Cl.
| | |
|---|---|
| C12P 7/46 | (2006.01) |
| C12R 1/01 | (2006.01) |
| C12N 9/10 | (2006.01) |
| C12N 9/16 | (2006.01) |
| C12P 7/18 | (2006.01) |
| C12P 7/42 | (2006.01) |

(52) U.S. Cl.
CPC ............ *C12R 1/01* (2013.01); *C12N 9/1051* (2013.01); *C12N 9/16* (2013.01); *C12P 7/18* (2013.01); *C12P 7/42* (2013.01); *C12P 7/46* (2013.01); *C12Y 301/03024* (2013.01)

(58) Field of Classification Search
None
See application file for complete search history.

(56) References Cited

U.S. PATENT DOCUMENTS

| | | | | |
|---|---|---|---|---|
| 5,792,630 A | * | 8/1998 | Tonouchi | C12N 9/1051 435/101 |
| 6,960,455 B2 | | 11/2005 | Livshits | |
| 7,179,623 B2 | | 2/2007 | Livshits | |
| 2008/0275426 A1 | | 11/2008 | Bramucci | |
| 2009/0047719 A1 | | 2/2009 | Burgard | |
| 2009/0253192 A1 | | 10/2009 | Emptage | |
| 2009/0311756 A1 | | 12/2009 | Zelder | |
| 2010/0018417 A1 | | 1/2010 | Gervasi et al. | |

FOREIGN PATENT DOCUMENTS

| | | |
|---|---|---|
| WO | WO2010032698 A1 | 3/2010 |
| WO | WO2010053052 A1 | 5/2010 |
| WO | WO2010115067 A2 | 10/2010 |

OTHER PUBLICATIONS

Song et al. (Enzyme & Microbial Tech., vol. 39, 2006, pp. 352-361).*
Lee et al. (Biotech. & Bioengin. vol. 72, No. 1, 2001).*
Lee et al. (Applied &Environ. Microbiol., Mar. 2006, vol. 72, No. 3, pp. 1939-1948).*
Chan et al. (Bioresource Technology, vol. 103, 2012, pp. 329-336).*
Roa et al. (Applied Microbiol. Biotechnol., vol. 78, 2008, pp. 379-389).*
Alaeddinoglu, N. G., and Charles, H. P., Transfer of a gene for sucrose utilization into *Escherichia coli* K12, and consequent failure of expression of genes for D-serine utilization. J. Gen. Microbiol., 1979, 110, 47-59.
Bachmann, B. J., Pedigrees of some mutant strains of *Escherichia coli* K-12. Bacteriol. Rev., 1972, 36, 525-557.
Becker, J., Klopproggei, C., Zelder, O., Heinzle, E., and Wittmann, C., Amplified expression of fructose 1,6-Bisphosphatase in *Corynebacterium glutamicum* increases in vivo flux through the pentose phosphate pathway and lysine production on different carbon sources. Appl. Environ. Microbiol., 2005, 71: 8587-8596.
Bockmann, J., Heuel, H., and Lengler, J. W., Characterization of a chromosomally encoded, non-PTS metabolic pathway for sucrose utilization in *Escherichia coli* EC3132. Mol. Gen. Genet.,1992, 235, 22-32.

(Continued)

*Primary Examiner* — Hope Robinson
(74) *Attorney, Agent, or Firm* — Ramasamy M. Mannan

(57) ABSTRACT

This invention relates to the production of chemicals by fermentation with a microorganism in which the fermentation medium contains the sugar sucrose. As a specific example, succinic acid is produced from a sucrose-containing renewable feedstock through fermentation using a biocatalyst. Examples of such a biocatalyst include microorganisms that have been enhanced in their ability to utilize sucrose as a carbon and energy source. The biocatalysts of the present invention are derived from the genetic manipulation of parental strains that were originally constructed with the goal to produce one or more chemicals (for example succinic acid and/or a salt of succinic acid) at a commercial scale using feedstocks other than sucrose. The genetic manipulations of the present invention involve the introduction of exogenous genes involved in the transport and metabolism of sucrose into the parental strains. The genes involved in the transport and metabolism of sucrose can also be introduced into a microorganism prior to developing the organism to produce a particular chemical. The genes involved in the transport and metabolism of sucrose can also be used to augment or improve the sucrose transport and metabolism by strains already known to have some ability for sucrose utilization in biological fermentation.

11 Claims, 6 Drawing Sheets

(56) References Cited

OTHER PUBLICATIONS

Caescu, C., Vidal, O., Krewinski, F., Artenie, V., and Bouquelet, S., Bifidobacterium longum requires a fructokinase (Frk; ATP:D-fructose 6-phosphotransferase, EC 2.7.1.4) for fructose catabolism. J. Bacteriol., 2004, 186:6515-6525.

Datsenko, K. A., and Wanner, B. L., One-step inactivation of chromosomal genes in Escherichia coli K-12 using PCR products. Proc. Natl. Acad. Sci. U. S. A., 2000, 97, 6640-6645.

Deutscher, J., Francke, C., and Postma, P. W., How phosphotransferase system-related protein phosphorylation regulates carbohydrate metabolism in bacteria. Microbio. Mol. Bio. Rev., 2006 70: 939-1031.

Doelle, H. W., Kinetic characgteristics and regulatory mechanisms of glucokinase and fructokinase from Zymomonas mobilis. European J. Appl. Microbiol. Biotechnol., 1982, 14: 241-246.

Dominquez, H., and Lindley, N. D., Complete sucrose metabolism requires fructose phosphotransferase activity in Corynebacterium glutamicum to ensure phosphorylation of liberated fructose. Appl. Environ. Microbiol., 1996, 62: 3878-3880.

Engels, V., Linden, S. N., and Wendisc, V. F., The global repressor SugR controls expression of genes of glycolysis and of the L-lactate dehydrogenase LdHA in Corynebacterium glutamicum. J. Bacteriol., 2008. 190: 8033-8044.

Goedl, C., Schwartz, A., Minani, A., and Nidetzky, B., Recombinant sucrose phosphorylase from Leuconostoc mesenteroides: characterization, kinetic studies of transglucosylation, and application of immobilised enzyme for production of alpha-D-glucose 1-phosphate. J Biotechnol., 2007, 129, 77-86.

Han, B., Liu, H., Hu, X., Cai, Y., Zheng, D., Yuan, Z., Molecular characterization of a glucokinase with broad hexose specificity from Bacillus sphaericus strain C3-41. Appl. Environ. Microbiol., 2007, 73: 3581-3586.

Hernandez_Monyalvo, V., Martinez, A., Hernandez-Chavez, G., Boliar, F., Valle, F., Gosset, G., Expression of galp and glk in a Eschericahi coli PTS mutant restores glucose transport and increases glycolyitc flux to fermentation products. Biotechnol. Bioengineer., 2003, 83: 687-694.

Hugouvieux-Cotte-Pattat, N., and Charaoui-Boukerzaza, S., Catabolism of raffinose, sucrose, and melibiose in Erwinia chrysanthemi 3937. J. Bacteriol., 2009, 191: 6960-6967.

Jahreis, K., Bentler, L., Bockmann, J., Hans, S., Meyer, A., Siepelmeyer, J., and Lengeler, J. W., Adaptation of sucrose metabolism in the Escherichia coli wild type strain EC3132. J. Bacteriol., 2002, 184: 5307-5316.

Jankovic, I., and Bruckner, R., Carbon catabolite repression of sucrose utilization in Staphylococcus xylosus: Catabolite control protein CcpA ensures glucose preference and autoregulatory limitation of sucrose utilization. J. Mol. Microbiol. Biotechnol., 2007, 12: 114-120.

Jantama, K., Haupt, MJ., Svvoronos, S. A., Zhang, X., Moore, JC. Shanmugham, K. T., and Ingram, L. O., Combining metabolic engineering and metabolic evolution to develop nonrecombinant strains of Escherichia coli.

Jantama, K., Zhang, X., Moore, JC., Shanmugham, K. T., Svoronos, S. A., and Ingram, L. O., Eliminating side products and increasing succinate yields in engineered strains of Escherichia coli C, Biotechnol. Bioeng., 2008, 101, 881-893.

Jiang, L., Cai, J., Wang, J., Liang, S., Xu, Z. and Yang, S. T., Phosphoenolpyruvate-dependent phosphorylation of sucrose by clostridium tyrobutyricum ZJU 8235: evidence for the phosphotransferase transport system. Bioresour. Technol., 2010, 101: 304-9.

Lee, J., Mitchell, W. J., Tangney, M., and Blaschek, H. P., Evidence for the presence of an alternative glucose transport system in clostridium beijerinckii NCIMB 8052 and the solvent-hyperproduciing mutant BA101. Appl. Environ. Microbiol., 2005, 71: 3384-3387.

Lee, J. W., Choi, S., Park, J. H., Vickers, C. E., Nielsen, L. K., and Lee, S. Y., Development of sucrose-utilizing Escherichia coli K-12 strain by cloning beta-fructofuranosidases and its application for L-threonine production. Appl Microbiol Biotechnol., 2010, 88, 905-913.

Lee, J. W., Choi, S., Kim, J. M., and Lee, S. Y., Mannheimia succiniproducens phosphotransferase system for sucrose utilization. App. Environ. Microbiol., 2010, 76: 1699-1703.

Moon, M-W., Kim, H-J., O. H., T-K., Shin, C-S., Lee, J-S., Kim, S-J., and Lee, J-K., Analyses of enzyme II gene mutants for sugar transport and heterologus expression of fructokinase gene in Corynebacterium glutamicum ATCC 13032. FEMS Mirobiol. Lett., 2005, 244: 259-266.

Neidhardt, F. C., and Curtiss, R., Escherichia coli and Salmonella : cellular and molecular biology, 2nd ed., ASM Press, Washington, D.C. 1966.

Reid, S. J., and Abratt, V. R. Sucrose utilization in bacteria: genetic organization and regulation. Appl. Microbiol. Biotechnol., 2005, 67: 312-321.

Reizer, J., Bachem, S., Reizer, A., Arnaud, M., Saier Jr., MH., and Stulke, J., Novel phosphotransferase system genes revealed by genome analysis—the complete complements of PTS proteins encoded within the genome of Bacillus subtilis. Microbiology, 1999, 145: 3419-3429.

Scholten, E., Renz, T, and Thomas, J., Continuous cultivation approach for fermentative succinic acid production from crude glycerol by Basfia succiniciproducens DD1. Biotechnol. Lett., 2009, 31:1947-1951.

Shukla, V. B., Zhou, S., Yomano, L. P., Shanmugham, K. T., Preston, J. F., Ingram, L. O., Production of D(−)-lactate from sucrose and molasses. Biotechnol. Lett., 2004, 26: 689-693.

Tanaka, Y., Okai, N., Termoto, H., Inui, M., and Yukawa, H., Regulation of the expression of phosphoenolpyruvate: Carbohydrate phosphotransferase system (PTS) genes in Corynebacterium glutamicum R. Microbiol., 2008, 154: 264-274.

Tangney, M., Yazdanian, M., and Mitchell, W. J., Sucrose transport and metabolism in Clostridium beijerinickii. J. Appl. Microbiol., 1998, 84: 914-9.

Tangney, M. and Mitchell W. J., Analysis of a catabolic operon for sucrose transport and metabolism in Clostridium acetobutylicum ATCC 824. J. Mol. Microbiol. Biotechnol., 2002 2: 71-80.

Trindale, M. I., Abratt, V. R., and Reid, S. J., Induction of sucrose utilization genes from Bifidobacterium lactis by sucrose and raffinose. Appl. Environ. Microbiol., 2003, 69: 24-32.

Wang, J., Zhu, J., Bennett, G. N. and San, K-Y., Succinate production from different carbon sources under anaerobic conditions by metabolic engineered Escherichia coli strains. Metab. Eng., 2011, 13: 328-335.

Yi, J., Draths, KM., Li, K., and Frost JW., Altered glucose transport and shikimate pathway product yields in E. coli Biotechnol. Prog., 2003, 19: 1450-1459.

Zhang, X. Jantama, K., Moore JC, Jarboe, LR., Shanmugam, KT., and Ingram, O., Metabolic evolution of energy-conserving pathway for succinate production of Escherichia coli. Proc. Natl. Acad. Sci. USA, 2009, 106: 20180-20185.

Zhang, X., Jantama, K., Shanmugam, K. T., Ingram, L. O., Re-engineering Escherichia coli for succinate production in mineral salts medium. App Environ Microbiol., 2009, 75: 7807-7813.

Bruschi, M., Boyes, S. J., Sugiarto, H., Nielsen, L. K., Vickers, C. E., A transferable sucrose utilization approach for non-sucrose-utilizing Escherichia coli strains. Biotech. Adv., 2012, 30: 1001-1010.

Chan, S., Kanchanatawee, S., Jantama, Kaemwich., Production of succinic acid from sucrose and sugarcane molasses by metabolically engineered Escherichia coli. Biore. Tech. 2012, 103: 329-336.

* cited by examiner

SEQUENCE LISTING

<160> NUMBER OF SEQ ID NOS: 15

<210> SEQ ID NO 1
<211> LENGTH: 71
<212> TYPE: DNA
<213> ORGANISM: Artificial Sequence
<220> FEATURE:
<223> OTHER INFORMATION: PCR Primer SD032

<400> SEQUENCE: 1
taaatttcct cttgtcaggc cggaataact ccctataatg cgccaccact aggcgtttgg    60

```
attaggcgat t                                                           71

<210> SEQ ID NO 2
<211> LENGTH: 73
<212> TYPE: DNA
<213> ORGANISM: Artificial Sequence
<220> FEATURE:
<223> OTHER INFORMATION: PCR Primer SD033

<400> SEQUENCE: 2
ctcaggagaa ccccgctgac ccggcggcgt gtttgccgtt gttccgtgtc gatccgttgt      60
tccacctgat att                                                        73

<210> SEQ ID NO 3
<211> LENGTH: 20
<212> TYPE: DNA
<213> ORGANISM: Artificial Sequence
<220> FEATURE:
<223> OTHER INFORMATION: PCR Primer SD034

<400> SEQUENCE: 3
ttagtatgcc accaggaagt                                                  20

<210> SEQ ID NO 4
<211> LENGTH: 20
<212> TYPE: DNA
<213> ORGANISM: Artificial Sequence
<220> FEATURE:
<223> OTHER INFORMATION: PCR Primer SD035

<400> SEQUENCE: 4
atgctcaaag aattaaactt                                                  20

<210> SEQ ID NO 5
<211> LENGTH: 20
<212> TYPE: DNA
<213> ORGANISM: Artificial Sequence
<220> FEATURE:
<223> OTHER INFORMATION: PCR Primer SD036

<400> SEQUENCE: 5
cagttttctt cgcaatttcg                                                  20

<210> SEQ ID NO 6
<211> LENGTH: 20
<212> TYPE: DNA
<213> ORGANISM: Artificial Sequence
<220> FEATURE:
<223> OTHER INFORMATION: PCR Primer SD037

<400> SEQUENCE: 6
gacacgctcg ccctaaggat                                                  20

<210> SEQ ID NO 7
<211> LENGTH: 72
<212> TYPE: DNA
<213> ORGANISM: Artificial Sequence
<220> FEATURE:
<223> OTHER INFORMATION: PCR Primer SD038

<400> SEQUENCE: 7
tggaaagtcc tgtggataaa tcgggaaaat ctgtgagaaa cagaagatct gagcgactgt      60
accagaacat ga                                                         72
```

<210> SEQ ID NO 8
<211> LENGTH: 69
<212> TYPE: DNA
<213> ORGANISM: Artificial Sequence
<220> FEATURE:
<223> OTHER INFORMATION: PCR Primer SD039

<400> SEQUENCE: 8
agatcctgca aaacgatcgg gaccgcggat catagcctaa actgcgcaag tcgccgtaat    60
gggctttga                                                           69

<210> SEQ ID NO 9
<211> LENGTH: 31
<212> TYPE: DNA
<213> ORGANISM: Artificial Sequence
<220> FEATURE:
<223> OTHER INFORMATION: PCR Priimer BY83

<400> SEQUENCE: 9
ttacctagag agggtgagaa ttgccgaaca t                                   31

<210> SEQ ID NO 10
<211> LENGTH: 32
<212> TYPE: DNA
<213> ORGANISM: Artificial Sequence
<220> FEATURE:
<223> OTHER INFORMATION: PCR Priimer BY84

<400> SEQUENCE: 10
gatgagagaa gattttcagc ctgatacaga tt                                  32

<210> SEQ ID NO 11
<211> LENGTH: 45
<212> TYPE: DNA
<213> ORGANISM: Artificial Sequence
<220> FEATURE:
<223> OTHER INFORMATION: PCR Primer BY107

<400> SEQUENCE: 11
gggtctagaa tagtggagga ataataatgg aaattcaaaa caaag                    45

<210> SEQ ID NO 12
<211> LENGTH: 43
<212> TYPE: DNA
<213> ORGANISM: Artificial Sequence
<220> FEATURE:
<223> OTHER INFORMATION: PCR Primer BY108

<400> SEQUENCE: 12
cgcggatcct tgtctgtcaa tataatattt cccactatca gca                      43

<210> SEQ ID NO 13
<211> LENGTH: 5772
<212> TYPE: DNA
<213> ORGANISM: Escherichia coli
<220> FEATURE:
<221> NAME/KEY: misc_feature
<223> OTHER INFORMATION: pMH17F - Plasmid clone of thrV region,
      spectinomycin resistance

<400> SEQUENCE: 13
gttgacagta agacgggtaa gcctgttgat gataccgctg ccttactggg tgcattagcc    60
agtctgaatg acctgtcacg ggataatccg aagtggtcag actggaaaat cagagggcag   120
gaactgctga acagcaaaaa gtcagatagc accacatagc agacccgcca taaaacgccc   180

```
tgagaagccc gtgacgggct tttcttgtat tatgggtagt ttccttgcat gaatccataa      240
aaggcgcctg tagtgccatt taccccatt cactgccaga gccgtgagcg cagcgaactg       300
aatgtcacga aaagacagc gactcaggtg cctgatggtc ggagacaaaa ggaatattca       360
gcgatttgcc cgagcttgcg agggtgctac ttaagccttt agggttttaa ggtctgtttt      420
gtagaggagc aaacagcgtt tgcgacatcc ttttgtaata ctgcggaact gactaaagta      480
gtgagttata cacagggctg ggatctattc tttttatctt tttttattct ttctttattc      540
tataaattat aaccacttga atataaacaa aaaaaacaca caaaggtcta gcggaattta      600
cagagggtct agcagaattt acaagttttc cagcaaaggt ctagcagaat ttacagatac      660
ccacaactca aggaaaagg actagtaatt atcattgact agcccatctc aattggtata       720
gtgattaaaa tcacctagac caattgagat gtatgtctga attagttgtt ttcaaagcaa      780
atgaactagc gattagtcgc tatgacttaa cggagcatga aaccaagcta attttatgct      840
gtgtggcact actcaacccc acgattgaaa accctacaag gaaagaacgg acggtatcgt      900
tcacttataa ccaatacgct cagatgatga acatcagtag ggaaaatgct tatggtgtat      960
tagctaaagc aaccagagag ctgatgacga gaactgtgga aatcaggaat cctttggtta     1020
aaggctttga gattttccag tggacaaact atgccaagtt ctcaagcgaa aaattagaat     1080 tagttttag tgaagagata ttgccttatc ttttccagtt aaaaaaattc ataaatata       1140 atctggaaca tgttaagtct tttgaaaaca aatactctat gaggatttat gagtggttat     1200
taaaagaact aacacaaaag aaaactcaca aggcaaatat agagattagc cttgatgaat     1260
ttaagttcat gttaatgctt gaaaataact accatgagtt taaaaggctt aaccaatggg     1320
ttttgaaacc aataagtaaa gatttaaaca cttacagcaa tatgaaattg gtggttgata     1380
agcgaggccg cccgactgat acgttgattt tccaagttga actagataga caaatggatc     1440
tcgtaaccga acttgagaac aaccagataa aaatgaatgg tgacaaaata ccaacaacca     1500
ttacatcaga ttcctaccta cgtaacggac taagaaaaac actacacgat gctttaactg     1560
caaaaattca gctcaccagt tttgaggcaa aatttttgag tgacatgcaa agtaagcatg     1620
atctcaatgg ttcgttctca tggctcacgc aaaaacaacg aaccacacta gagaacatac     1680
tggctaaata cggaaggatc tgaggttctt atggctcttg tatctatcag tgaagcatca     1740
agactaacaa acaaaagtag aacaactgtt caccgttaga tatcaaaggg aaaactgtcc     1800
atatgcacag atgaaaacgg tgtaaaaaag atagatacat cagagctttt acgagttttt     1860
ggtgcattta aagctgttca ccatgaacag atcgacaatg taacagatga acagcatgta     1920
acacctaata gaacaggtga aaccagtaaa acaaagcaac tagaacatga aattgaacac     1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa     2100
tcatggcaat tctggaagaa atagcgcttt cagccggcaa acctgaagcc ggatctgcga     2160
ttctgataac aaactagcaa caccagaaca gcccgtttgc gggcagcaaa acccgttatg     2220
cttgtaaacc gttttgtgaa aaatttttta aataaaaaa ggggacctct agggtcccca     2280
attaattagt aatataatct attaaaggtc attcaaaagg tcatccaccg gatcaattcc     2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460
gcaaaccctc actgatccgc atgcccgttc catacagaag ctgggcgaac aaacgatgct     2520
```

```
cgccttccag aaaaccgagg atgcgaacca cttcatccgg ggtcagcacc accggcaagc   2580
gccgcgacgg ccgaggtctt ccgatctcct gaagccaggg cagatccgtg cacagcacct   2640
tgccgtagaa gaacagcaag gccgccaatg cctgacgatg cgtggagacc gaaaccttgc   2700
gctcgttcgc cagccaggac agaaatgcct cgacttcgct gctgcccaag gttgccgggt   2760
gacgcacacc gtggaaacgg atgaaggcac gaacccagtg gacataagcc tgttcggttc   2820
gtaagctgta atgcaagtag cgtatgcgct cacgcaactg gtccagaacc ttgaccgaac   2880
gcagcggtgg taacggcgca gtggcggttt tcatggcttg ttatgactgt ttttttgggg   2940
tacagtctat gcctcgggca tccaagcagc aagcgcgtta cgccgtgggt cgatgtttga   3000
tgttatggag cagcaacgat gttacgcagc agggcagtcg ccctaaaaca aagttaaaca   3060
tcatgaggga agcggtgatc gccgaagtat cgactcaact atcagaggta gttggcgtca   3120
tcgagcgcca tctcgaaccg acgttgctgg ccgtacattt gtacggctcc gcagtggatg   3180
gcggcctgaa gccacacagt gatattgatt tgctggttac ggtgaccgta aggcttgatg   3240
aaacaacgcg gcgagctttg atcaacgacc ttttggaaac ttcggcttcc cctggagaga   3300
gcgagattct ccgcgctgta gaagtcacca ttgttgtgca cgacgacatc attccgtggc   3360
gttatccagc taagcgcgaa ctgcaatttg gagaatggca gcgcaatgac attcttgcag   3420
gtatcttcga gccagccacg atcgacattg atctggctat cttgctgaca aaagcaagag   3480
aacatagcgt tgccttggta ggtccagcgg cggaggaact ctttgatccg gttcctgaac   3540
aggatctatt tgaggcgcta aatgaaacct taacgctatg gaactcgccg cccgactggg   3600
ctggcgatga gcgaaatgta gtgcttacgt tgtcccgcat ttggtacagc gcagtaaccg   3660
gcaaaatcgc gccgaaggat gtcgctgccg actgggcaat ggagcgcctg ccggcccagt   3720
atcagcccgt catacttgaa gctagacagg cttatcttgg acaagaagaa gatcgcttgg   3780
cctcgcgcgc agatcagttg gaagaatttg tccactacgt gaaaggcgag atcaccaagg   3840
tagtcggcaa ataatgtcta acaattcgtt caagccgacg ccgcttcgcg gcgcggctta   3900
actcaagcgt tagatgcact aagcacataa ttgctcacag ccaaactatc aggtcaagtc   3960
tgcttttatt ttttttaagc gtgcataata agccctacac aaattgggag atatatcatg   4020
aaaggctggc ttttttcttgt tatcgcaata gttggcgaag taatcgcaac atccgcatta   4080
aaatctagcg agggctttac taagctgatc cggtggatga cctttttgaat gacctttaat   4140 agattatatt actaattaat tggggaccct agaggtcccc ttttttattt taaaaatttt   4200
ttcacaaaac ggtttacaag catacgttgg ccgattcatt aatgcagctg gcacgacagg   4260
tttcccgact ggaaagcggg cagtgagcgc aacgcaatta atgtgagtta gctcactcat   4320
taggcacccc aggctttaca ctttatgctt ccggctcgta tgttgtgtgg aattgtgagt   4380
tacctagaga gggtgagaat tgccgaacat gcgcataagt ttcccggaca gatttcaggt   4440
ggtcagcagc aacgcgttgc cattgcgcgt tcgctgtgta tgaagccgaa aattatgttg   4500
tttgatgagc caacgtcggc gctcgatcct gagatggtga agaggtgct ggatacgatg   4560 attgggctgg cgcagtcggg tatgacaatg ttgtgtgtaa cacatgagat ggggtttgca   4620
cgaaccgtcg ctgaccgggt aattttttatg gatcgtgggg aaatagtgga gcaagctgca   4680
cctgatgaat tttttgcgca tcctaaatca gagcgtacga gggcatttt atcgcaggta   4740 atccattaat tgaatgttag ttcgaaaagc aaaaaggcca tccttcggga tggcctttcg   4800
cttgatttga tgtctggcag tttatggcgg gcgtcctgcc cgccaccctc cgggccgttg   4860
cttcgcaacg ttcaaatccg ctcccggcgg atttgtccta ctcgggagag tgttcaccga   4920
```

```
caaacaacag ataaaacaaa aggcccagtc ttccgactga gccttttgtt ttatttgatg      4980
tctggcagtt ccctactctc gcatggggag accccacact accatcggcg ctacggcggt      5040
ttcacttctg agttcggcat ggggtcaggt gggaccaccg cgctactgcc gccagacaaa      5100
ttcttttcta atctgccgaa ctttaaccta aaaagtggtg ctgataccca gagtcgaact      5160
ggggacctca cccttaccaa gggtgcgctc taccaactga gccatatcag cacgctaaat      5220
ttgatgcctg gcagttccct actctcgcat ggggagaccc cacactacca tcggcgctac      5280
ggcgtttcac ttctgagttc ggcatggggt caggtgggac caccgcgcta cggccgccag      5340
gcaaattctg ttttatcaga ccgcttctgc gttctgattt aatctgtatc aggctgaaaa      5400
tcttctctca tccggataac aatttcacac aggaaacagc tatgaccatg attacgccaa      5460
gctgtaccga gctcgaattc actggccgtc gttttacaac gtcgtgactg ggaaaaccct      5520
ggcgttaccc aacttaatcg ccttgcagca catccccctt tcgccagctg gcgtaatagc      5580
gaagaggccc gcaccgatcg cccttcccaa cagttgcgca gcctgaatgg cgaatggcgc      5640
ctgatgcggt attttctcct tacgcatctg tgcggtattt cacaccgcat atggtgcact      5700
ctcagtacaa tctgctctga tgccgcatag ttaagccagc cccgacaccc gccaacaccc      5760
gctgacgaat tc                                                          5772
```

<210> SEQ ID NO 14
<211> LENGTH: 7558
<212> TYPE: DNA
<213> ORGANISM: Leuconostoc mesenteroides
<220> FEATURE:
<221> NAME/KEY: misc_feature
<223> OTHER INFORMATION: Plasmid DNA pRY802F with sucrose phosphorylase
      gene driven by constitutive promoter for integration at teh thrV
      locus.

<400> SEQUENCE: 14

```
gttgacagta agacgggtaa gcctgttgat gataccgctg ccttactggg tgcattagcc       60
agtctgaatg acctgtcacg ggataatccg aagtggtcag actggaaaat cagagggcag      120
gaactgctga acagcaaaaa gtcagatagc accacatagc agacccgcca taaaacgccc      180
tgagaagccc gtgacgggct tttcttgtat tatgggtagt ttccttgcat gaatccataa      240
aaggcgcctg tagtgccatt taccccatt cactgccaga gccgtgagcg cagcgaactg      300
aatgtcacga aaagacagc gactcaggtg cctgatggtc ggagacaaaa ggaatattca      360
gcgatttgcc cgagcttgcg agggtgctac ttaagccttt agggttttaa ggtctgtttt      420
gtagaggagc aaacagcgtt tgcgacatcc ttttgtaata ctgcggaact gactaaagta      480
gtgagttata cacagggctg ggatctattc tttttatctt tttttattct ttctttattc      540
tataaattat aaccacttga atataaacaa aaaaaacaca caaggtctta gcggaattta      600
cagagggtct agcagaattt acaagttttc cagcaaaggt ctagcagaat ttacagatac      660
ccacaactca aggaaaagg actagtaatt atcattgact agcccatctc aattggtata      720
gtgattaaaa tcacctagac caattgagat gtatgtctga attagttgtt ttcaaagcaa      780
atgaactagc gattagtcgc tatgacttaa cggagcatga aaccaagcta attttatgct      840
gtgtggcact actcaacccc acgattgaaa accctacaag gaaagaacgg acggtatcgt      900
tcacttataa ccaatacgct cagatgatga acatcagtag ggaaaatgct tatggtgtat      960
tagctaaagc aaccagagag ctgatgacga gaactgtgga atcaggaat cctttggtta     1020 aaggctttga gattttccag tggacaaact atgccaagtt ctcaagcgaa aaattagaat     1080
```

```
tagtttttag tgaagagata ttgccttatc ttttccagtt aaaaaaattc ataaaatata    1140
atctggaaca tgttaagtct tttgaaaaca aatactctat gaggatttat gagtggttat    1200
taaaagaact aacacaaaag aaaactcaca aggcaaatat agagattagc cttgatgaat    1260
ttaagttcat gttaatgctt gaaaataact accatgagtt taaaaggctt aaccaatggg    1320
ttttgaaacc aataagtaaa gatttaaaca cttacagcaa tatgaaattg gtggttgata    1380
agcgaggccg cccgactgat acgttgattt tccaagttga actagataga caaatggatc    1440
tcgtaaccga acttgagaac aaccagataa aaatgaatgg tgacaaaata ccaacaacca    1500
ttacatcaga ttcctaccta cgtaacggac taagaaaaac actacacgat gctttaactg    1560
caaaaattca gctcaccagt tttgaggcaa aattttttgag tgacatgcaa agtaagcatg    1620
atctcaatgg ttcgttctca tggctcacgc aaaaacaacg aaccacacta gagaacatac    1680 tggctaaaata cggaaggatc tgaggttctt atggctcttg tatctatcag tgaagcatca    1740
agactaacaa acaaaagtag aacaactgtt caccgttaga tatcaaaggg aaaactgtcc    1800
atatgcacag atgaaaacgg tgtaaaaaag atagatacat cagagctttt acgagttttt    1860
ggtgcattta aagctgttca ccatgaacag atcgacaatg taacagatga acagcatgta    1920
acacctaata gaacaggtga aaccagtaaa acaaagcaac tagaacatga aattgaacac    1980
ctgagacaac ttgttacagc tcaacagtca cacatagaca gcctgaaaca ggcgatgctg    2040
cttatcgaat caaagctgcc gacaacacgg gagccagtga cgcctcccgt ggggaaaaaa    2100
tcatggcaat tctggaagaa atagcgcttt cagccggcaa acctgaagcc ggatctgcga    2160
ttctgataac aaactagcaa caccagaaca gcccgtttgc gggcagcaaa accgttatg     2220 cttgtaaacc gttttgtgaa aaatttttta aataaaaaaa ggggacctct agggtcccca    2280
attaattagt aatataatct attaaaggtc attcaaaagg tcatccaccg gatcaattcc    2340
cctgctcgcg caggctgggt gccaagctct cgggtaacat caaggcccga tccttggagc    2400
ccttgccctc ccgcacgatg atcgtgccgt gatcgaaatc cagatccttg acccgcagtt    2460
gcaaaccctc actgatccgc atgcccgttc catacagaag ctgggcgaac aaacgatgct    2520
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt ttttttgggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
```

```
gtatcttcga gccagccacg atcgacattg atctggctat cttgctgaca aaagcaagag    3480
aacatagcgt tgccttggta ggtccagcgg cggaggaact cttttgatcc ggttcctgaac   3540 aggatctatt tgaggcgcta atgaaacct taacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttttaagc gtgcataata agccctacac aaattgggag atatatcatg    4020
aaaggctggc tttttcttgt tatcgcaata gttggcgaag taatcgcaac atccgcatta    4080
aaatctagcg agggctttac taagctgatc cggtggatga cctttgaat gacctttaat     4140 agattatatt actaattaat tggggaccct agaggtcccc tttttattt taaaattt        4200 ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagt    4380
tacctagaga gggtgagaat tgccgaacat gcgcataagt ttcccggaca gatttcaggt    4440
ggtcagcagc aacgcgttgc cattgcgcgt tcgctgtgta tgaagccgaa aattatgttg    4500
tttgatgagc caacgtcggc gctcgatcct gagatggtga agaggtgct ggatacgatg     4560 attgggctgg cgcagtcggg tatgacaatg ttgtgtgtaa cacatgagat ggggtttgca    4620
cgaaccgtcg ctgaccgggt aattttatg gatcgtgggg aaatagtgga gcaagctgca     4680
cctgatgaat ttttgcgca tcctaaatca gagcgtacga gggcatttt atcgcaggta       4740 atccattaat tgaatgttag ttcgaaaagc aaaaaggcca tccttcgga tggcctttcg      4800 cttgatttga tgtctggcag tttatggcgg gcgtcctgcc cgccacctc cgggccgttg     4860 cttcgcaacg ttcaaatccg tcgaggctat tgacgacagc tatggttcac tgtccaccaa    4920
ccaaaactgt gctcagtacc gccaatattt ctcccttgag gggtacaaag aggtgtccct    4980
agaagagatc cacgctgtgt aaaaatttta caaaaggta ttgactttcc ctacaggtg       5040 tgtaataatt taattacagg cggggggcaac ccgcctgtt ctagaatagt ggaggaataa    5100
taatggaaat tcaaaacaaa gcaatgttga tcacttatgc tgattcgttg ggcaaaaact    5160
taaaagatgt tcatcaagtc ttgaaagaag atattggaga tgcgattggt ggggttcatt    5220
tgttgccttt cttcccttca acaggtgatc gcggttttgc gccagccgat tatactcgtg    5280
ttgatgccgc atttggtgat tgggcagatg tcgaagcatt gggtgaagaa tactatttga    5340
tgtttgactt catgattaac catatttctc gtgaatcagt gatgtatcaa gatttaagaa    5400
agaatcatga cgattcaaag tataaagatt tctttattcg ttgggaaaag ttctgggcaa    5460
aggccggcga aaccgtccaa cacaagccg atgttgactt aatttacaag cgtaaagata    5520
aggcaccaac gcaagaaatc acttttgatg atggcacaac agaaaacttg tggaatactt    5580
ttggtgaaga acaaattgac attgatgtta attcagccat tgccaaggaa tttattaaga    5640
caacccttga agacatggta aaacatggtg ctaacttgat tcgtttggat gcctttgcgt    5700
atgcagttaa aaaagttgac acaaatgact tcttcgttga gccagaaatc tgggacactt    5760
tgaatgaagt acgtgaaatt ttgacaccat taaaggctga aattttacca gaaattcatg    5820
```

```
aacattactc aatccctaaa aagatcaatg atcatggtta cttcacctat gactttgcat    5880
taccaatgac aacgctttac acattgtatt caggtaagca aaatcaattg gcaaagtggt    5940
tgaagatgtc accaatgaag caattcacaa cattggacac gcatgatggt attggtgtcg    6000
ttgatgcccg tgatattcta actgatgatg aaattgacta cgcttctgaa caactttaca    6060
aggttggcgc gaatgtcaaa aagacatatt catctgcttc atacaacaac cttgatattt    6120
accaaattaa ctcaacttat tattcagcat tgggaaatga tgatgcagca tacttgttga    6180
gtcgtgtctt ccaagtcttt gcgcctggaa ttccacaaat ttattacgtt ggtttgttgg    6240
caggtgaaaa cgtatcgcg cttttggagt caactaaaga aggtcgtaat attaaccgtc    6300
attactatac gcgtgaagaa gttaagtcag aagttaagcg accagttgtt gctaacttat    6360
tgaagctatt gtcatggcgt aatgaaagcc ctgcatttga tttggctggc tcaatcacag    6420
ttgacacgcc aactgataca acaattgtgg tgacacgtca agatgaaaat ggtcaaaaca    6480
aagctgtatt aacagccgat gcggccaaca aaacttttga aatcgttgag aatggtcaaa    6540
ctgttatgag cagtgataat ttgactcaga actaaactat atttgaatca atttctaaga    6600
actgtttcct gagggaagca gttttttttgc tgatagtggg aaatattata ttgacagaca    6660
aggatcctcc cggcggattt gtcctactcg ggagagtgtt caccgacaaa caacagataa    6720
aacaaaaggc ccagtcttcc gactgagcct tttgttttat ttgatgtctg gcagttccct    6780
actctcgcat ggggagaccc cacactacca tcggcgctac ggcggtttca cttctgagtt    6840
cggcatgggg tcaggtggga ccaccgcgct actgccgcca gacaaattct tttctaatct    6900
gccgaacttt aacctaaaaa gtggtgctga tacccagagt cgaactgggg acctcaccct    6960
taccaagggt gcgctctacc aactgagcca tatcagcacg ctaaatttga tgcctggcag    7020
ttccctactc tcgcatgggg agaccccaca ctaccatcgg cgctacggcg tttcacttct    7080
gagttcggca tggggtcagg tgggaccacc gcgctacggc cgccaggcaa attctgtttt    7140
atcagaccgc ttctgcgttc tgatttaatc tgtatcaggc tgaaaatctt ctctcatccg    7200
gataacaatt tcacacagga aacagctatg accatgatta cgccaagctg taccgagctc    7260
gaattcactg gccgtcgttt tacaacgtcg tgactgggaa accctggcg ttacccaact    7320 taatcgcctt gcagcacatc cccctttcgc cagctggcgt aatagcgaag aggcccgcac    7380
cgatcgccct tcccaacagt tgcgcagcct gaatggcgaa tggcgcctga tgcggtattt    7440
tctccttacg catctgtgcg gtatttcaca ccgcatatgg tgcactctca gtacaatctg    7500
ctctgatgcc gcatagttaa gccagccccg acacccgcca cacccgctg acgaattc       7558
```

<210> SEQ ID NO 15
<211> LENGTH: 8998
<212> TYPE: DNA
<213> ORGANISM: Escherichia coli
<220> FEATURE:
<221> NAME/KEY: misc_feature
<223> OTHER INFORMATION: Plasmid pRY803F with cat-sacB cassete for
      integration at thrV locus
<220> FEATURE:
<221> NAME/KEY: misc_feature
<222> LOCATION: (5979)..(5979)
<223> OTHER INFORMATION: n used for a, c, g , or t.

<400> SEQUENCE: 15

```
gttgacagta agacgggtaa gcctgttgat gataccgctg ccttactggg tgcattagcc      60
agtctgaatg acctgtcacg ggataatccg aagtggtcag actggaaaat cagagggcag     120
```

```
gaactgctga acagcaaaaa gtcagatagc accacatagc agacccgcca taaaacgccc      180
tgagaagccc gtgacgggct tttcttgtat tatgggtagt ttccttgcat gaatccataa      240
aaggcgcctg tagtgccatt taccccatt cactgccaga gccgtgagcg cagcgaactg       300
aatgtcacga aaaagacagc gactcaggtg cctgatggtc ggagacaaaa ggaatattca      360
gcgatttgcc cgagcttgcg agggtgctac ttaagccttt agggttttaa ggtctgtttt      420
gtagaggagc aaacagcgtt tgcgacatcc ttttgtaata ctgcggaact gactaaagta      480
gtgagttata cacagggctg ggatctattc ttttatctt tttttattct ttctttattc       540
tataaattat aaccacttga atataaacaa aaaaaacaca caaaggtcta gcggaattta     600
cagagggtct agcagaattt acaagttttc agcaaaggt ctagcagaat ttacagatac      660
ccacaactca aaggaaaagg actagtaatt atcattgact agcccatctc aattggtata     720
gtgattaaaa tcacctagac caattgagat gtatgtctga attagttgtt ttcaaagcaa     780
atgaactagc gattagtcgc tatgacttaa cggagcatga aaccaagcta attttatgct     840
gtgtggcact actcaacccc acgattgaaa accctacaag gaagaacgg acggtatcgt      900 tcacttataa ccaatacgct cagatgatga acatcagtag ggaaaatgct tatggtgtat     960
tagctaaagc aaccagagag ctgatgacga gaactgtgga atcaggaat cctttggtta    1020 aaggctttga gattttccag tggacaaact atgccaagtt ctcaagcgaa aaattagaat     1080 tagttttttag tgaagagata ttgccttatc ttttccagtt aaaaaaattc ataaaatata    1140
atctggaaca tgttaagtct tttgaaaaca aatactctat gaggatttat gagtggttat     1200
taaaagaact aacacaaaag aaaactcaca aggcaaatat agagattagc cttgatgaat     1260
ttaagttcat gttaatgctt gaaaataact accatgagtt taaaaggctt aaccaatggg     1320
ttttgaaacc aataagtaaa gatttaaaca cttacagcaa tatgaaattg gtggttgata     1380
agcgaggccg cccgactgat acgttgattt tccaagttga actagataga caaatggatc     1440
tcgtaaccga acttgagaac aaccagataa aaatgaatgg tgacaaaata ccaacaacca     1500
ttacatcaga ttcctaccta cgtaacggac taagaaaaac actacacgat gctttaactg     1560
caaaaattca gctcaccagt tttgaggcaa aatttttgag tgacatgcaa agtaagcatg     1620
atctcaatgg ttcgttctca tggctcacgc aaaaacaacg aaccacacta gagaacatac     1680
tggctaaata cggaaggatc tgaggttctt atggctcttg tatctatcag tgaagcatca     1740
agactaacaa acaaaagtag aacaactgtt caccgttaga tatcaaaggg aaaactgtcc     1800
atatgcacag atgaaaacgg tgtaaaaaag atagatacat cagagctttt acgagttttt    1860
ggtgcattta agctgttca ccatgaacag atcgacaatg taacagatga acagcatgta      1920
acacctaata gaacaggtga aaccagtaaa acaaagcaac tagaacatga aattgaacac     1980
ctgagacaac ttgttacagc tcaacagtca cacatagaca gcctgaaaca ggcgatgctg     2040
cttatcgaat caaagctgcc gacaacacgg gagccagtga cgcctcccgt ggggaaaaaa     2100
tcatggcaat tctggaagaa atagcgcttt cagccggcaa acctgaagcc ggatctgcga     2160
ttctgataac aaactagcaa caccagaaca gcccgtttgc gggcagcaaa acccgttatg     2220
cttgtaaacc gttttgtgaa aaatttttta aataaaaaa ggggacctct agggtcccca     2280
attaattagt aatataatct attaaaggtc attcaaaagg tcatccaccg gatcaattcc     2340
cctgctcgcg caggctgggt gccaagctct cgggtaacat caaggcccga tccttggagc     2400
ccttgccctc ccgcacgatg atcgtgccgt gatcgaaatc cagatccttg acccgcagtt     2460 gcaaacccctc actgatccgc atgcccgttc catacagaag ctgggcgaac aaacgatgct     2520
```

```
cgccttccag aaaaccgagg atgcgaacca cttcatccgg ggtcagcacc accggcaagc    2580
gccgcgacgg ccgaggtctt ccgatctcct gaagccaggg cagatccgtg cacagcacct    2640
tgccgtagaa gaacagcaag gccgccaatg cctgacgatg cgtggagacc gaaaccttgc    2700
gctcgttcgc cagccaggac agaaatgcct cgacttcgct gctgcccaag gttgccgggt    2760
gacgcacacc gtggaaacgg atgaaggcac gaacccagtg gacataagcc tgttcggttc    2820
gtaagctgta atgcaagtag cgtatgcgct cacgcaactg gtccagaacc ttgaccgaac    2880
gcagcggtgg taacggcgca gtggcggttt tcatggcttg ttatgactgt tttttggggg    2940
tacagtctat gcctcgggca tccaagcagc aagcgcgtta cgccgtgggt cgatgtttga    3000
tgttatggag cagcaacgat gttacgcagc agggcagtcg ccctaaaaca aagttaaaca    3060
tcatgaggga agcggtgatc gccgaagtat cgactcaact atcagaggta gttggcgtca    3120
tcgagcgcca tctcgaaccg acgttgctgg ccgtacattt gtacggctcc gcagtggatg    3180
gcggcctgaa gccacacagt gatattgatt tgctggttac ggtgaccgta aggcttgatg    3240
aaacaacgcg gcgagctttg atcaacgacc ttttggaaac ttcggcttcc cctggagaga    3300
gcgagattct ccgcgctgta gaagtcacca ttgttgtgca cgacgacatc attccgtggc    3360
gttatccagc taagcgcgaa ctgcaatttg gagaatggca gcgcaatgac attcttgcag    3420
gtatcttcga gccagccacg atcgacattg atctggctat cttgctgaca aaagcaagag    3480
aacatagcgt tgccttggta ggtccagcgg cggaggaact ctttgatccg gttcctgaac    3540
aggatctatt tgaggcgcta aatgaaacct aacgctatg gaactcgccg cccgactggg    3600
ctggcgatga gcgaaatgta gtgcttacgt tgtcccgcat ttggtacagc gcagtaaccg    3660
gcaaaatcgc gccgaaggat gtcgctgccg actgggcaat ggagcgcctg ccggcccagt    3720
atcagcccgt catacttgaa gctagacagg cttatcttgg acaagaagaa gatcgcttgg    3780
cctcgcgcgc agatcagttg gaagaatttg tccactacgt gaaaggcgag atcaccaagg    3840
tagtcggcaa ataatgtcta acaattcgtt caagccgacg ccgcttcgcg gcgcggctta    3900
actcaagcgt tagatgcact aagcacataa ttgctcacag ccaaactatc aggtcaagtc    3960
tgcttttatt attttttaagc gtgcataata agccctacac aaattgggag atatatcatg    4020
aaaggctggc ttttttcttgt tatcgcaata gttggcgaag taatcgcaac atccgcatta    4080
aaatctagcg agggctttac taagctgatc cggtggatga ccttttgaat gacctttaat    4140
agattatatt actaattaat tggggaccct agaggtcccc ttttttattt taaaaatttt    4200
ttcacaaaac ggtttacaag catacgttgg ccgattcatt aatgcagctg gcacgacagg    4260
tttcccgact ggaaagcggg cagtgagcgc aacgcaatta atgtgagtta gctcactcat    4320
taggcacccc aggctttaca ctttatgctt ccggctcgta tgttgtgtgg aattgtgagt    4380
tacctagaga gggtgagaat tgccgaacat gcgcataagt ttcccggaca gatttcaggt    4440
ggtcagcagc aacgcgttgc cattgcgcgt tcgctgtgta tgaagccgaa aattatgttg    4500
tttgatgagc caacgtcggc gctcgatcct gagatggtga agaggtgct ggatacgatg    4560 attgggctgg cgcagtcggg tatgacaatg ttgtgtgtaa cacatgagat ggggtttgca    4620
cgaaccgtcg ctgaccgggt aattttttatg gatcgtgggg aaatagtgga gcaagctgca    4680
cctgatgaat ttttgcgca tcctaaatca gagcgtacga gggcattttt atcgcaggta    4740
atccattaat tgaatgttag ttcgaaaagc aaaaaggcca tcctttcgga tggccttcg    4800 cttgatttga tgtctggcag tttatggcgg gcgtcctgcc cgccaccctc cgggccgttg    4860
```

```
cttcgcaacg ttcaaatccg ctcgaattcc cgcgcccgat gaattgatcc gaagttccta    4920
ttctctagaa agtataggaa cttcgaattg tcgacaagct agcatgtgac ggaagatcac    4980
ttcgcagaat aaataaatcc tggtgtccct gttgataccg ggaagccctg ggccaacttt    5040
tggcgaaaat gagacgttga tcggcacgta agaggttcca actttcacca taatgaaata    5100
agatcactac cgggcgtatt ttttgagtta tcgagatttt caggagctaa ggaagctaaa    5160
atggagaaaa aaatcactgg atataccacc gttgatatat cccaatggca tcgtaaagaa    5220 catttttgagg catttcagtc agttgctcaa tgtacctata accagaccgt tcagctggat    5280
attacggcct ttttaaagac cgtaaagaaa aataagcaca gtttatcc ggcctttatt    5340 cacattcttg cccgcctgat gaatgctcat ccggaattcc gtatggcaat gaaagacggt    5400
gagctggtga tatgggatag tgttcaccct tgttacaccg ttttccatga gcaaactgaa    5460
acgttttcat cgctctggag tgaataccac gacgatttcc ggcagtttct acacatatat    5520
tcgcaagatg tggcgtgtta cggtgaaaac ctggcctatt ccctaaagg gtttattgag    5580 aatatgtttt tcgtctcagc caatccctgg gtgagtttca ccagttttga tttaaacgtg    5640
gccaatatgg acaacttctt cgccccgtt ttcaccatgg gcaaatatta tacgcaaggc    5700
gacaaggtgc tgatgccgct ggcgattcag gttcatcatg ccgtttgtga tggcttccat    5760
gtcggcagaa tgcttaatga attacaacag tactgcgatg agtggcaggg cggggcgtaa    5820 ttttttttaag gcagttattg gtgcccttaa acgcctggtg ctacgcctga ataagtgata    5880
ataagcggat gaatggcaga aattcgaaag caaattcgac ccggtcgtcg gttcagggca    5940
gggtcgttaa atagccgctt atgtctattg ctggtttant cggtacccgg ggatcgcggc    6000
cgcggaccgg atcccatcac atatacctgc cgttcactat tatttagtga aatgagatat    6060
tatgatattt tctgaattgt gattaaaaag gcaactttat gcccatgcaa cagaaactat    6120
aaaaaataca gagaatgaaa agaaacagat agattttta gttctttagg cccgtagtct    6180
gcaaatcctt ttatgatttt ctatcaaaca aagaggaaa atagaccagt tgcaatccaa    6240
acgagagtct aatagaatga ggtcgaaaag taaatcgcgc gggtttgtta ctgataaagc    6300
aggcaagacc taaatgtgt aaagggcaaa gtgtatactt tggcgtcacc ccttacatat    6360
tttaggtctt tttttattgt gcgtaactaa cttgccatct tcaaacagga gggctggaag    6420
aagcagaccg ctaacacagt acataaaaaa ggagacatga acgatgaaca tcaaaaagtt    6480
tgcaaaacaa gcaacagtat taacctttac taccgcactg ctggcaggag cgcaactca    6540 agcgtttgcg aaagaaacga accaaaagcc atataaggaa acatacgca tttcccatat    6600 tacacgccat gatatgctgc aaatccctga acagcaaaaa aatgaaaaat atcaagttcc    6660
tgaattcgat tcgtccacaa ttaaaaatat ctcttctgca aaaggcctgg acgtttggga    6720
cagctggcca ttacaaaacg ctgacggcac tgtcgcaaac tatcacggct accacatcgt    6780
ctttgcatta gccggagatc ctaaaaatgc ggatgacaca tcgatttaca tgttctatca    6840
aaaagtcggc gaaacttcta ttgacagctg gaaaaacgct ggccgcgtct ttaaagacag    6900
cgacaaattc gatgcaaatg attctatcct aaaagaccaa acacaagaat ggtcaggttc    6960
agccacattt acatctgacg gaaaaatccg tttattctac actgatttct ccggtaaaca    7020
ttacggcaaa caaacactga caactgcaca agttaacgta tcagcatcag acagctcttt    7080
gaacatcaac ggtgtagagg attataaatc aatctttgac ggtgacggaa aaacgtatca    7140
aaatgtacag cagttcatcg atgaaggcaa ctacagctca ggcgacaacc atacgctgag    7200
agatcctcac tacgtagaag ataaaggcca caaatactta gtatttgaag caaacactgg    7260
```

```
aactgaagat ggctaccaag gcgaagaatc tttatttaac aaagcatact atggcaaaag    7320
cacatcattc ttccgtcaag aaagtcaaaa acttctgcaa agcgataaaa aacgcacggc    7380
tgagttagca aacggcgctc tcggtatgat tgagctaaac gatgattaca cactgaaaaa    7440
agtgatgaaa ccgctgattg catctaacac agtaacagat gaaattgaac gcgcgaacgt    7500 cttaaaatg aacggcaaat ggtacctgtt cactgactcc cgcggatcaa aaatgacgat     7560
tgacggcatt acgtctaacg atatttacat gcttggttat gtttctaatt ctttaactgg    7620
cccatacaag ccgctgaaca aaactggcct tgtgttaaaa atggatcttg atcctaacga    7680 tgtaacctt acttactcac acttcgctgt acctcaagcg aaaggaaaca atgtcgtgat     7740
tacaagctat atgacaaaca gaggattcta cgcagacaaa caatcaacgt tgcgccgag    7800 cttcctgctg aacatcaaag gcaagaaaac atctgttgtc aaagacagca tccttgaaca    7860
aggacaatta acagttaaca aataaaaacg caaaagaaaa tgccaatatc ctattggcat    7920
tttcttttat ttcttccatt taaatggatg catgcgctag cggagtgtat actggcttac    7980
tatgttggca ctgatgaggg tgtcagtgaa gtgcttcatg tggcaggaga aaaaaggctg    8040
caccggtgcg tcagcagaat atgtgataca ggatatattc cgcttcctcg ctcactgact    8100
gctgagctcc cggcggattt gtcctactcg ggagagtgtt caccgacaaa caacagataa    8160
aacaaaaggc ccagtcttcc gactgagcct tttgttttat ttgatgtctg gcagttccct    8220
actctcgcat ggggagaccc cacactacca tcggcgctac ggcggtttca cttctgagtt    8280
cggcatgggg tcaggtggga ccaccgcgct actgccgcca gacaaattct tttctaatct    8340 gccgaactt aacctaaaaa gtggtgctga tacccagagt cgaactgggg acctcaccct    8400
taccaagggt gcgctctacc aactgagcca tatcagcacg ctaaatttga tgcctggcag    8460
ttccctactc tcgcatgggg agacccaca ctaccatcgg cgctacggcg tttcacttct     8520
gagttcggca tggggtcagg tgggaccacc gcgctacggc cgccaggcaa attctgtttt    8580
atcagaccgc ttctgcgttc tgatttaatc tgtatcaggc tgaaaatctt ctctcatccg    8640
gataacaatt tcacacagga aacagctatg accatgatta cgccaagctg taccgagctc    8700
gaattcactg gccgtcgttt tacaacgtcg tgactgggaa aaccctggcg ttacccaact    8760
taatcgcctt gcagcacatc cccctttcgc cagctggcgt aatagcgaag aggcccgcac    8820
cgatcgccct tcccaacagt tgcgcagcct gaatggcgaa tggcgcctga tgcggtattt    8880
tctccttacg catctgtgcg gtatttcaca ccgcatatgg tgcactctca gtacaatctg    8940
ctctgatgcc gcatagttaa gccagccccg acacccgcca acaccgctg acgaattc      8998
```

METHOD OF PRODUCING SUCCINIC ACID AND OTHER CHEMICALS USING SUCROSE-CONTAINING FEEDSTOCK

CROSS-REFERENCE TO RELATED APPLICATION

The application is the U.S. national stage application of International Patent Application No. PCT/US2011/064598, which claims the priority of the U.S. Provisional Application Ser. No. 61/458,446, filed on Dec. 13, 2010.

FIELD OF THE INVENTION

The present invention is in the field of producing specialty and commodity organic chemicals using biocatalysts that have been modified to increase their ability to use sucrose-containing feedstock. More specifically, the present invention is related to the genetic modifications required for sucrose transport and metabolism in the biological production of succinic acid and other chemicals.

BACKGROUND OF THE INVENTION

A large number of organic chemicals are currently derived from petrochemical feedstocks. There is a growing interest in producing many of these petrochemical-derived organic compounds through biological fermentation processes using renewable feedstock. The list of organic compounds that can be derived from renewable feedstock includes 1,4-diacids (succinic, fumaric, malic, glucaric, malonic, and maleic), 2,5-furan dicarboxylic acid, propionic acid, 3-hydroxy propionic acid, aspartic acid, glucaric acid, glutamic acid, itaconic acid, levulinic acid, 3-hydroxybutyrolactone, glycerol, sorbitol, xylitol, arabinitol. and butanediols such as 1,4 butanediol, 1,3-butanediol, and 2,3-butanediol. Besides these compounds, many other types of organic compounds including, but not limited to, amino acids, vitamins, alcohols (such as ethanol, n-propanol, isopropanol, n-butanol, isobutanol, and higher alcohols), fatty acids, esters of fatty acids, hydrocarbons, isoprenoids, turpenes, carotenoids, and amines can also be produced using renewable feedstocks. Any such compound shall be referred to herein as a "desired compound". However, for most of these desired compounds, a commercially attractive fermentation process that uses sucrose as a carbon source has not yet been developed.

Among these organic compounds that can be derived from renewable feedstock, succinic acid deserves a special mention. A number of microbial species including *Escherichia coli*, *Corynebacterium glutamicum* and *Brevibacteium flavum*, *Mannhemia succiniproducens*, *Basfia succiniproducens* and *Anaerobiospirilum succiniproducens* have been genetically manipulated for use as a biocatalyst in the production of succinic acid using renewable feedstocks. These biocatalysts have been shown to produce succinic acid in very high yield and productivity. Currently, succinic acid production using these biocatalysts is carried out using dextrose as the source of organic carbon.

There is a need to develop processes that use cheaper renewable feedstock in order to make the biological production of succinic acid to be competitive with succinic acid production from petrochemical feedstocks using purely chemical processes. Efforts are under way to use carbon sources derived from the hydrolysis of cellulosic materials as the feedstock for succinic acid production using a biocatalyst. However, the techniques for producing feedstock from cellulosic materials for biological fermentation are far from perfected at this time. Thus there is an immediate need for a cost-effective feedstock suitable for biological production of succinic acid. The price of various sugars varies with time and geographic location. In many part of the world, sucrose is less expensive than glucose most or all of the time, especially in tropical areas where sugarcane thrives.

Molasses derived from the sugarcane processing represents a cost-effective feedstock for any industrial fermentation. Molasses is inexpensive, readily available, and abundant. Molasses is rich in sucrose and there is a need to develop biocatalysts with the ability to use sucrose as the source of carbon in the fermentative production of succinic acid. In some cases, it will be preferable to use purified sucrose in the fermentation as a carbon source, for example when the fermentation product of interest must be highly purified, and where it is more cost effective to remove the non-sugar compounds from the molasses prior to fermentations. Purified sucrose in the form of "table sugar" has been produced for many years by well known methods, and material equivalent to this can also be used as carbon source in the present invention. In addition, molasses or sucrose utilization by biocatalysts has wider industrial significance as molasses or sucrose can be used to produce a wide variety of organic chemicals as well as whole cell mass. Thus the present invention has broader application in the fermentation industry in general beyond the fermentative production of succinic acid. A sucrose-containing medium can comprise juice or molasses derived from sugar cane, sugar beet, sweet sorghum, or any other sucrose-containing plant material.

A mechanism for the transport of sucrose and other sugars that is frequently found in bacteria is based on the phosphotransferase system (PTS). PTS is composed of two-energy-coupling proteins, Enzyme I and HPr, and several sugar-specific Enzyme II proteins or protein complexes, which typically consist of three protein domains, EIIA, EIIB and EIIC. The organization of the EII domains differs between bacteria. EII may consist of a single fused protein or different fused and unfused domains. The translocation of the specific sugar through the membrane is facilitated by the integral membrane domain. However, it is the complex of the three enzyme domains or proteins, functioning together, which brings about the transport and phosphorylation of the sugar substrate, resulting in an intracellular pool of phosphorylated carbohydrate (Neidhardt and Curtiss, 1996).

There are alternative mechanisms for bacterial sucrose transport in addition to the PTS. These PTS-independent sugar permeases facilitate sucrose accumulation without chemical modifications. They include solute-cation symport systems, such as the ScrT symporter in the sucrose operon in *Bifidobacerium lactis* and the CscB transporter of *E. coli* W strain. These sucrose-specific transport systems are generally clustered with the catabolic and regulatory genes in various arrangements in different bacteria.

There are several examples in the literature that describe the cloning of sucrose utilization genes and the installation of such genes into organisms that did not natively contain said genes. There are examples of cloning and transfer of both PTS-dependent and PTS-independent sucrose utilization genes. However, each of these examples has at least one feature that makes them undesirable for use in a commercial setting. For example, maintenance of sucrose utilization genes on replicating plasmids (such as the pScr1 plasmid described in US Patent Application Publication No. 2008/0274526 A1) is not desirable because plasmids can be unstable (Shukla et al., 2004) or lost during the many generations of large scale growth, and they often require presence of an antibiotic for maintenance. Also, expression of a gene from a multicopy plasmid can be excessive, leading to waste of energy and materials, or inhibition of growth.

The chromosomal PTS-independent sucrose utilization genes cscAKB from *E. coli* EC3132 have been integrated into the chromosome of *E. coli* K-12 derived strains (U.S. Pat. No. 6,960,455). But this particular operon is known to be relatively inefficient at conferring sucrose utilization, especially at low sucrose concentrations, where the doubling time was 20 hours (1200 minutes) (Bockmann et al., 1992). A homology comparison of the DNA sequence of the cscRAKB operon region from EC3132 with that of an efficient sucrose utilizer, *E. coli* ATCC 9637 (Shukla et al., 2004) using the Megalign program of DNASTAR software revealed a similarity index of 98.1. Thus there were many differences between the two csc operons, and these differences are scattered throughout the operon. Many of the point mutations in the EC3132 operon cause non-conservative changes in protein sequences, and some of the mutations were in promoter regions, so it must be the case that the operon from EC3132 is simply defective due to one or more of these mutations. Faster growing spontaneous mutants with a doubling time on sucrose of down to 50 minutes could be isolated from EC3132, but when the mutated cscAKB operons were installed in a K-12 strain, the doubling time on sucrose medium increased back up to 75 minutes at best (Jahreis et al., 2002). None of the mutated csc operons from EC3132 changed the DNA sequence to be more like the efficient operon of ATCC 9637. As such, it appears that the operon disclosed by Jahreis et al (2002) is not as desirable as that of ATCC 9637.

Another approach that has been proposed to enable sucrose utilization is to simply engineer a strain to secrete invertase (Lee et al., 2010a). In this case the invertase from *Mannheimia succiniproducens* was shown to be superior to the invertase from *E. coli* W, teaching away from the use of the *E. coli* W invertase. Moreover, in bacteria, this approach is inherently less efficient than importing the sucrose before cleaving it, since after cleavage to glucose and fructose by invertase, two sugar molecules must be imported rather than just one, and this requires more energy to be expended. Moreover, in this prior art example, during fermentation starting with 20 g/l sucrose, external fructose accumulated to over 10 g/l, and it took 50 hours for this external fructose to be completely consumed (Lee et al., 2010b). Thus, although a sucrose utilizing strain was disclosed, the system had performance characteristics that were not commercially attractive. Secretion of fructose by *E. coli* strains grown on sucrose is a general problem, and the fructose that remains at the end of a desirable fermentation time, which is often 48 hours or less, is undesirable. Thus, there is a need for microorganisms that can ferment sucrose to a desirable product at a commercially attractive titer, which is usually more than 20 grams per liter, without leaving more than 2 grams per liter of fructose remaining after a fermentation time of 48 hours or less.

*E. coli* strains SZ63 and SZ85 were previously engineered to produce optically pure D-lactate from hexose and pentose sugars. To expand the substrate range to include sucrose, a cscR'AKB operon was cloned and characterized from *E. coli* KO11, a derivative of *E. coli* W (Shukla et al., 2004). The resulting plasmid-borne operon was functionally expressed in SZ63 but was unstable in SZ85.

U.S. Pat. No. 6,960,455 discloses a method of producing amino acids using *E. coli* K-12 derived strains transduced with a cscRAKB operon from strain EC3132 that is located at the dsdA locus in the chromosome. As a consequence of insertion of cscRKAB operon at this location in the chromosome, the resulting strains cannot catabolize D-serine. As pointed out above, the csc genes used in this prior art were derived from a defective EC3132 operon, which grows poorly on low concentrations of sucrose (Bockmann et al., 1992; Jahreis et al, 2002). The resulting strains contain the cscR gene, which encodes a repressor, so the strains are expected to be suboptimal for sucrose utilization, especially in the presence of glucose, which would be expected to cause repression of the cscAKB genes (Jahreis et al., 2002; Shukla et al., 2004). Molasses usually contains some glucose. There was no attempt mentioned to correct any of the defects inherent in the csc operon of EC3132 in U.S. Pat. No. 6,960,455. Moreover, production of chemicals other than amino acids, such as succinate were not mentioned in this patent.

U.S. Pat. No. 7,179,623 discloses a strain constructed from a sucrose non-assimilative strain wherein the said strain harbors sucrose PTS genes from *E. coli* VKPM B-7915 (scrKYABR genes), but again, this patent does not mention production of chemicals other than amino acids, and the PTS-dependent system claimed in this disclosure is not optimal for production of chemicals that are derived from phosphoenol pyruvate (PEP).

SUMMARY OF THE INVENTION

This present invention provides biocatalysts and a method for using sucrose-containing renewable biological feedstock in the fermentative production of commercially important products, for example, but not limited to specialty and commodity chemicals. Specifically, the present invention is useful in the fermentative production of organic acids using sucrose-containing renewable feedstocks. More specifically, the present invention is useful in the fermentative production of succinic acid from a sucrose-containing renewable feedstock using biocatalysts that have been constructed to have improved sucrose utilization. The principles of the present invention can be applied to many other desired chemical compounds that can be produced by fermentation, particularly fumaric acid and malic acid.

According to the present invention, the genes coding for the proteins involved in sucrose transport and metabolism can be introduced into a wide variety of biocatalysts either to confer a new ability to the biocatalyst to utilize sucrose as a source of carbon and energy in the fermentation medium, or to augment or improve an already existing capacity of the biocatalysts for sucrose transport and metabolism.

In one embodiment, the present invention improves the ability to import and metabolize sucrose by a biocatalyst that has been previously constructed to produce a chemical such as succinic acid in commercially significant quantities, wherein said biocatalyst did not originally have the ability to efficiently use sucrose as the source of organic carbon for the fermentative production of a chemical of commercial interest such as succinic acid. In one aspect of the present invention, the inability or poor ability of the original biocatalyst to use sucrose stems from the absence of genes coding for the sucrose transport and metabolism. In another aspect, the inability of the biocatalyst to use sucrose results from the unintended consequence of genetic manipulations aimed at improving the succinic acid yield and productivity in the fermentation medium in which the majority of the organic carbon source is other than sucrose. In another aspect, the inability of the biocatalyst to use sucrose results from one or more defects in the native sucrose utilization system that render the system unable to achieve commercially attractive utilization of sucrose for fermentation using sucrose-containing medium. The present invention provides genetic solutions to overcome any of these aspects of genetic deficiency in sucrose utilization.

In another embodiment, the present invention aims at augmenting the sucrose utilization capacity of the biocatalysts used in the production of succinic acid. The present invention augments the sucrose utilization by the biocatalyst by means of improving the capacity for sucrose transport and metabolism through genetic manipulations. In one aspect of the present invention, the already existing sucrose transport capacity of the biocatalyst is improved by the introduction of genes coding for the proteins involved in a PTS-dependent mechanism for sucrose uptake. In another aspect, the present invention provides additional genes coding for the proteins associated with a PTS-independent sucrose permease system such as a cation symport sucrose permease system to augment the already existing sucrose transport capacity of the biocatalyst. In yet another aspect, the present invention augments the sucrose utilization by means of providing genes coding for the metabolism of the sucrose transported into the cell.

In another aspect, the present invention provides a process for producing succinic acid in a sucrose-containing medium which makes use of a biocatalyst which has retained a functional PEP-dependent phosphotransferase system for sugar uptake.

The utilization of sucrose in the production of succinic acid by the biocatalyst involves the participation of a number of proteins responsible for the conversion of sucrose into three carbon intermediates that can enter into the tricarboxylic acid cycle and ultimately yield succinic acid. In one aspect, the present invention genetically enhances the activity of one or more enzymes involved in the conversion of sucrose into six carbon intermediates that can be further metabolized by common biochemical pathways. In addition to sucrose transporters, the enzyme targets suitable for genetic manipulation are selected from a list consisting of sucrose phosphorylase, sucrose hydrolase (invertase), sucrose-6-phosphate hydrolase, glucose kinase (glucokinase), and fructose kinase (fructokinase).

In another embodiment, the present invention provides a process for producing succinic acid using sucrose as a renewable feedstock. In one aspect, the present invention provides a process for producing succinic acid in a sucrose-containing medium which makes use of a biocatalyst that has decreased activity in the PEP-dependent phosphotransferase system.

In one aspect, the present invention discloses the addition of genes to an organism such as to install or increase the activity of one or more proteins and/or enzymes involved in the import and conversion of sucrose into metabolic intermediates such as fructose 1,6-bisphosphate that can be further metabolized by the cell. The genes that encode relevant proteins or enzymes suitable for genetic manipulation of this invention are one, or a combination of more than one genes selected from a list consisting of genes that encode a PTS-dependent sucrose importer (a PTS protein usually named Enzyme $II^{scr}$, or $EII^{scr}$, that functions together with other PTS proteins to accomplish the import and phosphorylation of sucrose to give cytoplasmic sucrose-6-phosphate), sucrose-6-phosphate hydrolase, sucrose permease (a PTS-independent permease that transports sucrose into the cell without concomitant phosphorylation), invertase or sucrose hydrolase, sucrose phosphorylase, glucose kinase (glucokinase), fructose kinase (fructokinase), hexose-phosphate isomerase, and phosphofructo kinase (fructose-1-phosphate kinase).

In another embodiment, the present invention provides a process for producing succinic acid or other chemicals using sucrose as a renewable feedstock. In one aspect, the present invention provides a process for producing succinic acid in a sucrose-containing medium which makes use of a biocatalyst that has a decreased activity in at least one protein of the organism's native PTS system relative to that of the ancestral or parental strain. In another aspect, the present invention provides a process for producing succinic acid or other chemical in a sucrose-containing medium which makes use of a biocatalyst which has retained a fully functional PTS-dependent phosphotransferase system for sugar uptake.

The novel aspects of this invention are that the cscABK genes from a non-pathogenic, robust sucrose utilizer have been stably integrated into the chromosome of a bacterium, such that the newly constructed bacterium can produce a commercial product in a commercially viable process. The titer of product from sucrose is equal to at least the titer produced by the parent organism from glucose, and the yield of product is greater than 0.8 g/g sugar. The cscABK operon is integrated at a site in the chromosome that does not interfere with any relevant aspect of growth or production of desired products.

Additional advantages of this invention will become readily apparent from the ensuing description.

DETAILED DESCRIPTION OF THE PREFERRED EMBODIMENTS

Figure 1:
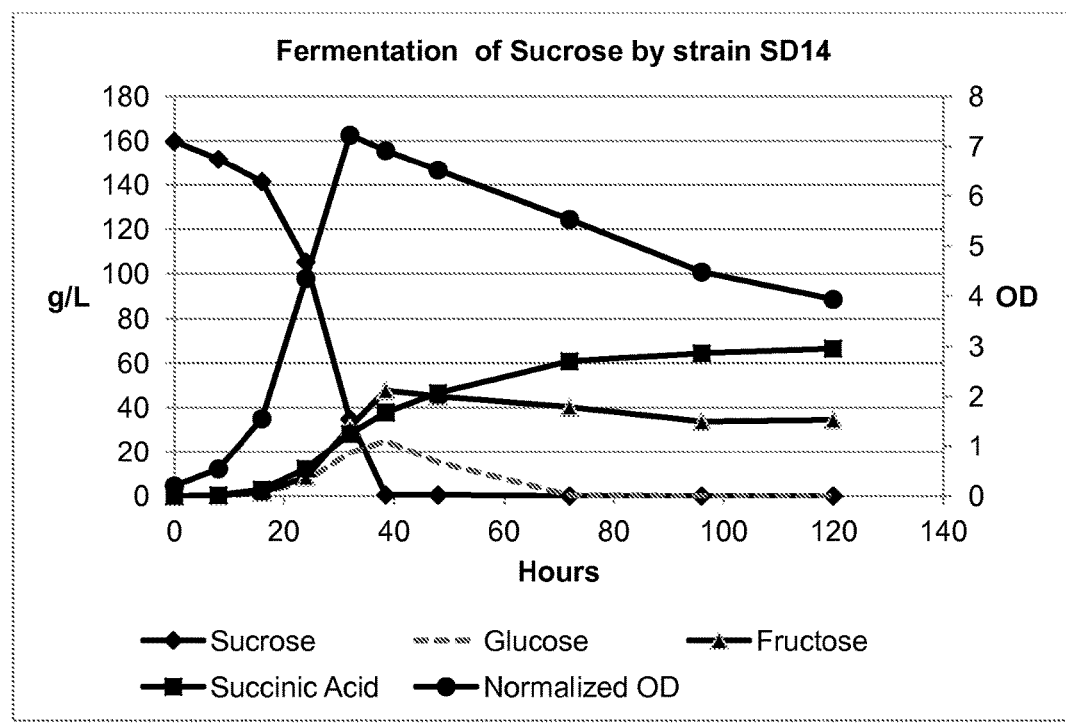
FIG. 1. Kinetics of sucrose utilization and succinic acid production by the SD14 strain of *E. coli* grown in minimal medium supplemented with 10% sucrose (w/w). For FIGS. 1-5, fermentations were done in small microaerobic fermentors as described in Jantama et al (2008a), except that the volume was 300 ml and neutralization was accomplished with a solution containing 2.4 M potassium carbonate and 1.2 M potassium hydroxide.
Figure 2:
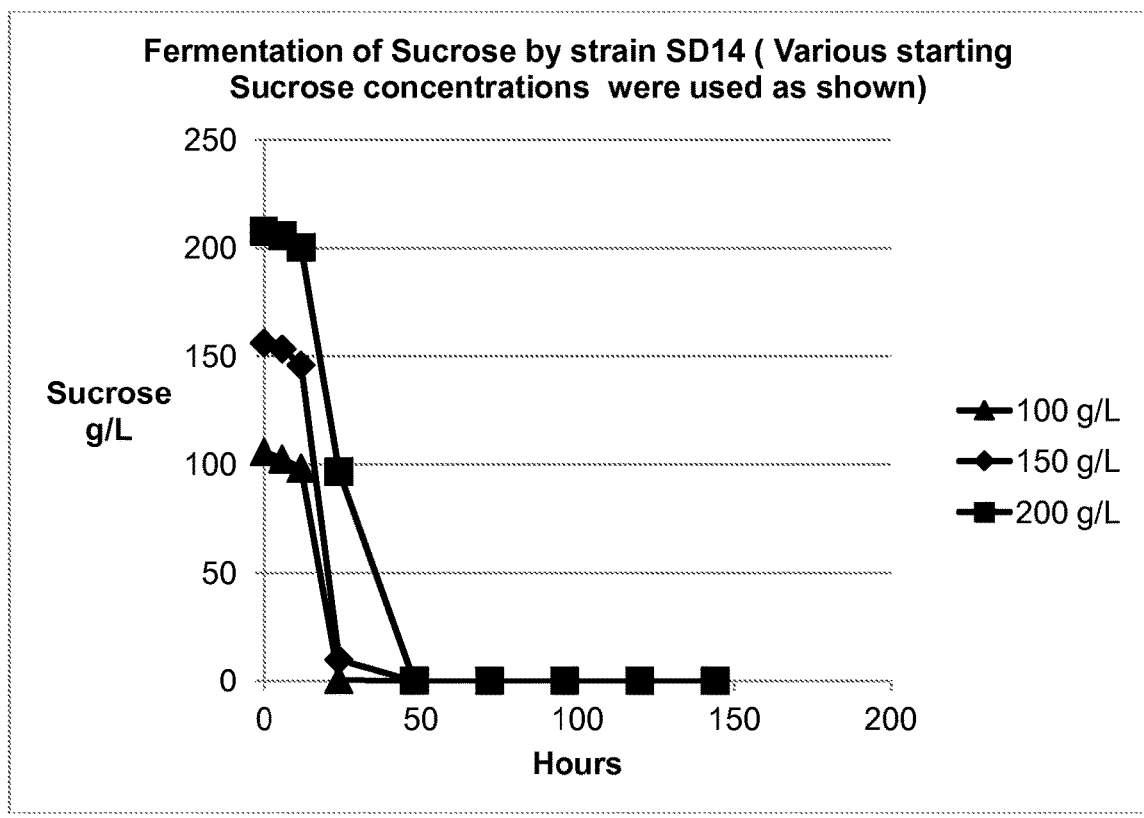
FIG. 2. Kinetics of sucrose utilization in three different experiments with varying concentrations of initial sucrose concentrations. Initial concentrations 100 g/L, 150 g/L and 200 g/L of sucrose were used. The SD14 strain of *E. coli* was used in these experiments.
Figure 3:
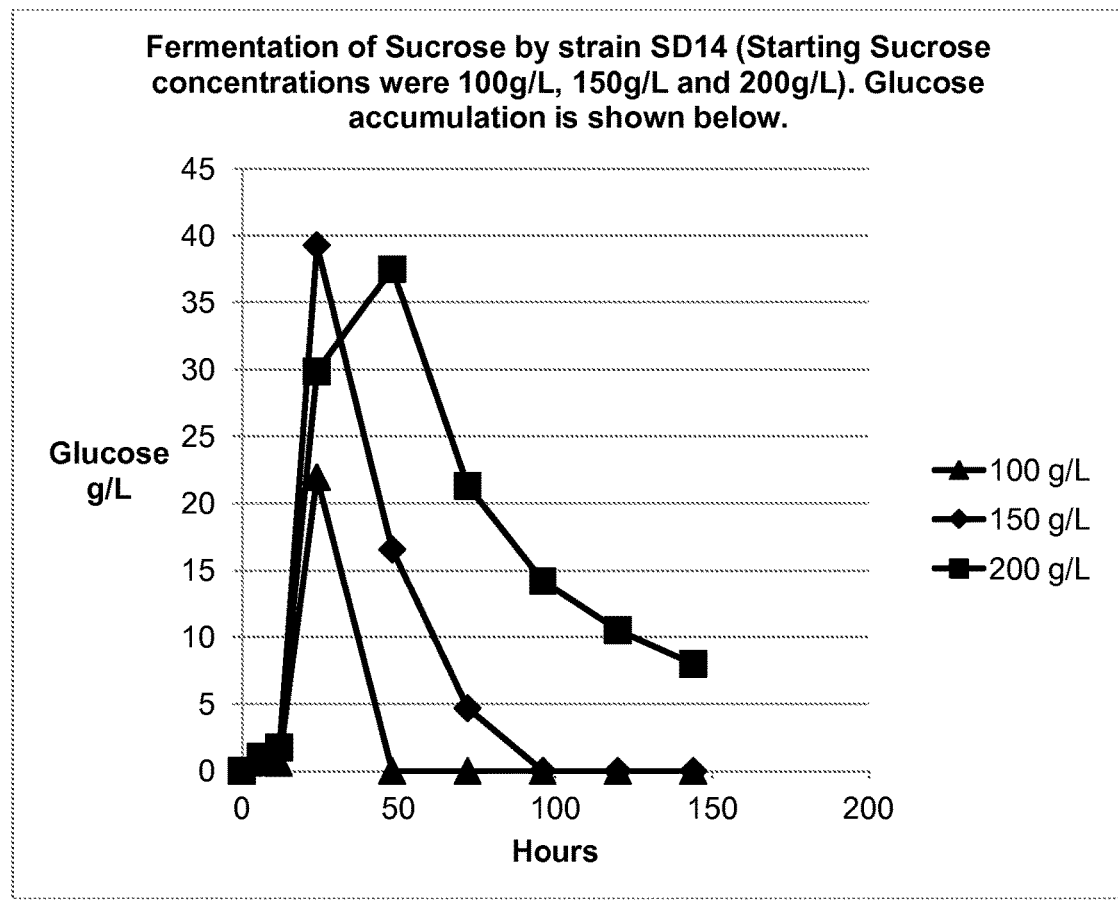
FIG. 3. Kinetics of change in the glucose concentration in the growth medium during the fermentative production of succinic acid. The fermentation medium contained sucrose as the source of organic carbon. Initial concentrations 100 g/L, 150 g/L and 200 g/L of sucrose were used. The SD14 strain of *E. coli* was used in this experiment.
Figure 4:
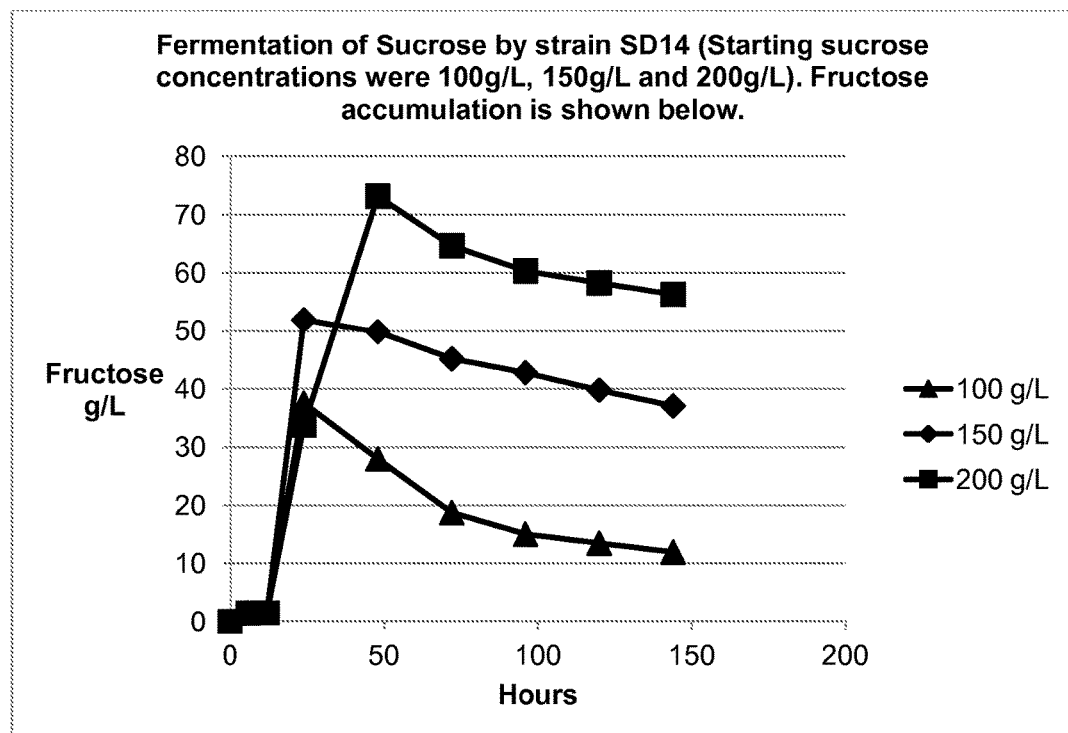
FIG. 4. Kinetics of change in the fructose concentration in the growth medium during the fermentative production of succinic acid. The fermentation medium contained sucrose as the source of organic carbon. Initial concentrations 100 g/L, 150 g/L and 200 g/L of sucrose were used. The SD14 strain of *E. coli* was used in this experiment.
Figure 5:
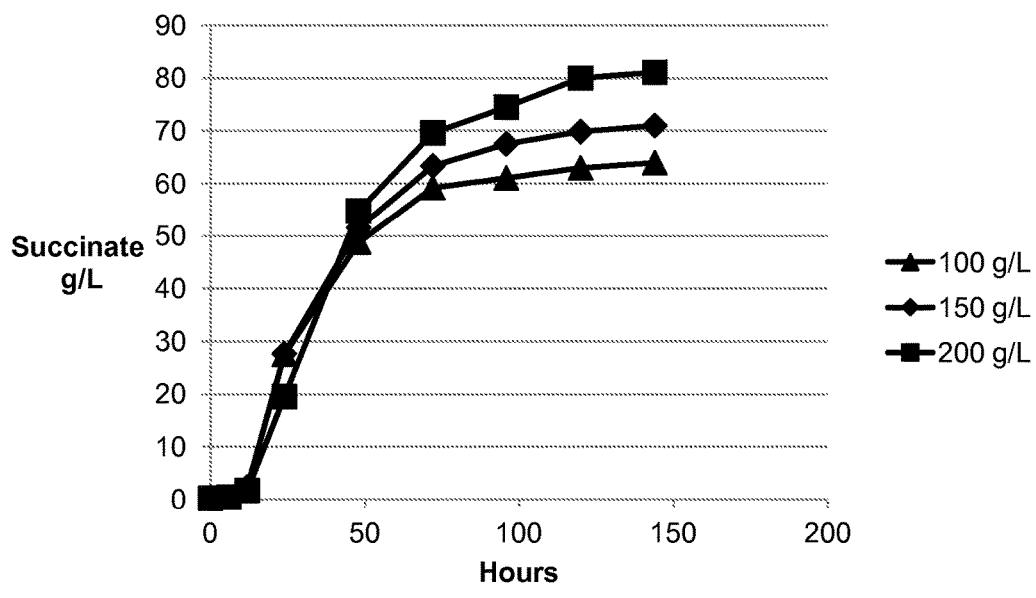
FIG. 5. Kinetics of succinic acid accumulation in the growth medium. Initial concentrations 100 g/L, 150 g/L and 200 g/L of sucrose were used. The SD14 strain of *E. coli* was used in this experiment.

The present invention provides biocatalysts for succinic acid production in high titer, yield and productivity using sucrose-containing feedstock. Sucrose is a disaccharide also known as saccharose, 1-O-α-D-glucopyranosyl-β-D-fructo-furanoside, and α-D-glucopyranosyl-1,2-β-D-fructofurano-side. The term "yield" as defined in this invention refers to the number of grams of product (such as succinic acid) produced per gram of sugar (such as glucose or sucrose) consumed. The term "productivity" as defined in this present invention refers to the number of grams of product (such as succinic acid) produced per liter of culture per hour. The term "titer" is defined as the concentration of product (such as succinic acid) in the fermentation broth in grams per liter. The desirable yield for succinic acid is in the range of 0.7-1.2 grams of succinic acid produced per gram of sugar consumed. The desirable productivity for succinic acid in this present invention is in the range of 1 gram or more of succinic acid produced per liter per hour.

For any given compound, it might be more appropriate to produce a salt of said compound, so for example, succinic acid might be produced at pH near 7 as a salt of sodium, potassium, calcium, magnesium, ammonium, etc., while lysine might be produced as a salt of chloride, sulfate, bicarbonate, etc. As such, any time a compound is named herein, any salt of said compound is meant to be included, and any time a salt is named, the free acid or free base is also meant to be included.

The bacterial growth rate is measured in terms of the rate of increase in the optical density at 550 or 600 nanometers of the liquid culture resulting from the bacterial multiplication. The bacterial growth rate is also expressed in terms of time required for doubling of bacterial cells. The wild type E. coli bacterial cells are reported to replicate once in every 20 minutes. In the bacterial cells suitable for the present investigation, the bacterial cells are expected to have a doubling time of at least 20 minutes, but less than 20 hours.

According to the present invention, the biocatalyst for succinic acid production can be developed in two different ways. Under the first approach, selected wild type bacterial species is genetically manipulated to grow with the sucrose as the sole source of carbon. It is preferable that the genetically manipulated bacterial strain while acquiring the ability to grow well in a medium containing sucrose as the sole carbon source, still retains the ability to use other carbon sources equally well. Once a particular microbial strain with the ability to grow on sucrose as the sole source of carbon is identified, subsequent genetic manipulations are carried out in the metabolic pathways following the genetic engineering methods known in the art to obtain a bacterial strain which could grow on sucrose containing medium and produce succinic acid with high yield and productivity. For example, the patent applications published under Patent Cooperation Treaty with the publication No. WO 2010/115067 and United States Patent Application Publication No. US 20100184171 provide the details about the genetic engineering techniques useful in generating a strain of E. coli with improved succinic acid production capacity. These two patent applications are incorporated herein by reference.

Under the second approach, a bacterial strain already developed to have a commercially attractive yield and productivity for succinic acid production as described in the patent application publications US 20100184171 and WO 2010/115067 is used as a parental strain. Further genetic manipulations are carried out with this strain to obtain a bacterial strain that has the ability to grow in a sucrose-containing media and produces succinic acid at a commercially attractive titer, yield, and productivity.

More specifically, this present invention is focused on developing a biocatalyst that retains its original ability to produce succinic acid at high enough titer and productivity while gaining the new ability to grow in a medium containing sucrose as a major source of carbon. For example, the KJ122 strain of E. coli described by Jantama et al (2008 a, b) can be selected as the starting strain for the present invention. The KJ122 strain of E. coli is reported to have the ability to produce succinic acid in a minimal glucose medium at high titer and productivity. The term "minimal medium" shall mean a medium that contains only mineral salts, a purified carbon source (such as glucose or sucrose) and betaine. A "minimal medium" does not contain any rich or chemically undefined components such as peptides or nucleotides, such as are found in yeast extract, tryptone, peptone, corn steep liquor, or other hydrolysates of complex biological material. A minimal medium can be in liquid or solid form, as in agar plates. A minimal medium may have one or more purified compounds, such as vitamins or amino acids, added to satisfy a specific growth requirement of a particular strain. The KJ122 strain of E. coli was derived from the E. coli C strain through gene deletions and metabolic evolution as described in US Patent Application Publication No. US 20100184171 and in the patent application published on Oct. 7 Apr. 2, 2010 under Patent Cooperation Treaty with the publication No. WO 2010/115067 A1. These two patent application publication documents providing details about the genetic changes that led to the development of the KJ122 strain of E. coli are incorporated herein by reference. KJ122 does not have any substantial ability to use sucrose as a source of carbon in the production of succinic acid. This deficiency in sucrose utilization noted in KJ122 is attributable to the genetic deficiency in its parental strain, namely the E. coli C strain which is known to be genetically deficient in sucrose utilization.

The term "sucrose utilization" as used in this application includes both the transport of the sucrose from the growth medium into the bacterial cells and the subsequent metabolism of the sucrose within the cell. The substantial inability of KJ122 to transport and metabolize sucrose stems from the lack of the genes coding for both sucrose transport and metabolism. The inventors have discovered genetic approaches that would enable KJ122 to utilize sucrose as a source of carbohydrate while retaining its original ability to produce succinic acid at high titer, yield, and productivity.

The term "carbohydrate" as used in this invention includes mono-saccharides such as glucose, fructose, xylose, and arabinose, disaccharides such as sucrose, melibi-ose, maltose and lactose, trisaccharides such as raffinose and maltotriose, and higher oligosaccarodes, and hydrolysates derived from the enzymatic or chemical digestion of polysaccharides such as starch, cellulose, and hemicellulose.

Sucrose transport into bacterial cells, and the subsequent metabolism of sucrose, can be mediated by at least four different mechanisms, including a phosphoenolpyruvate (PEP) dependent phosphotransferase system (PTS) and three PTS independent systems, including a cation symport sucrose permease system. According to the present invention, it is possible to genetically alter either any of these sucrose transport and utilization systems with a goal either to confer a new ability to utilize sucrose or to enhance the already existing sucrose utilization capacity. The term "sucrose utilization function" as used in this invention refers to both sucrose uptake function and metabolism of sucrose within the cell. The sucrose metabolism within the cell involve conversion of sucrose into three carbon compounds that could enter into synthesis of commercially important organic compounds.

The terms "PTS+ organism" or "PTS+ bacterium" refers to a bacterium which has the capacity for sucrose transport based on a PTS. The term "non-PTS organism," or "non-PTS bacterium" refers to bacterial cells whose sucrose uptake capacity is based on the transport mechanisms other than PTS. Similarly, the term "non-PTS sucrose transport" refers to the transport of sucrose across the bacterial cell membrane using a mechanism other than PEP dependent PTS. The term "PTS− organism" means an organism that has a mutation in one or more genes that encode a protein that functions in PTS, such that the activity of the PTS is decreased relative to that of the wild type PTS. The term "sucrose permease" as used in the present invention includes the proteins involved in the uptake of the sucrose from the medium into the cell. The proteins involved in the sucrose uptake may be a component of PTS or a protein not associated with PTS.

One type of system starts by importing the sucrose into the cell by a phosphotransferase system (PTS) that uses phosphoenolpyruvate (PEP) as the source of energy and phosphate, and which phosphorylates the sucrose in the process of transport. We shall call this type of sucrose import and metabolism system a "PTS-dependent" system or mechanism. In this first type of system, there is a protein component that has useful or specific affinity for sucrose. This protein is called, among other names, Enzyme $II^{scr}$. Enzyme $II^{scr}$ functions together with two other proteins that are not specific for sucrose, called the common PTS sub-units. These said other proteins (proteins common to more than one specific PTS in a particular organism) include proteins that are named, among other names, EI and Hpr. In $Escherichia\ coli$ ($E.\ coli$), the genes encoding these general protein components are named, among other names, ptsH and ptsI. Most bacteria have several PTS proteins that are different from Enzyme $II^{scr}$, that are not specific to sucrose, but which are specific to other sugars (such as glucose, mannose, etc.), and which can function together with the common PTS subunits in the import of said other sugars. The genes and proteins that constitute a PTS are found in a wide variety of bacterial genera and species. Many such genes and proteins are homologous to the ones found in $E.\ coli$, but some are not very homologous, if at all, to their $E.\ coli$ counterparts. An example of this first type of sucrose transport system (PTS-dependent) is the system encoded by the scrKYABR genes of, for example, bacteria of the genus $Klebsiella$ and the Gram-negative plasmid pUR400 (Reid and Abratt, 2005). In these operons, scrK encodes a fructokinase, scrY encodes a sucrose specific outer membrane porin, scrA encodes a PTS Enzyme $II^{scr}$ transport protein, scrB encodes a sucrose-6-phosphate hydrolase, and scrR encodes a repressor.

A second type of sucrose transport system does not directly use PEP as an energy source or phosphate donor, but instead uses proton (or other cation) symport as a source of energy to carry sucrose into the cell without concomitant phosphorylation. We shall call this type of sucrose transport and metabolism system a "PTS-independent" system. An example of this second type is the system encoded by the chromosomal cscRAKB genes present in some, but not all, strains of $E.\ coli$ near the dsdA (D-serine deaminase) locus. Examples of $E.\ coli$ strains that contain the cscRAKB genes are EC3132 (Bockman et al., 1992) and ATCC 9637, also known as $E.\ coli$ W or the Waksman strain (Shukla et al., 2004). Note that there is some confusion in the literature as to the identity of the family of strains described in Shukla et al (2004). In the publication by Shukla et al (2004), the parent strain named KO11 was described as being derived form ATCC 11303 or $E.\ coli$ B, but in reality the strain is derived from ATCC 9637. In this type of operon, cscA encodes an invertase, cscB encodes a sucrose symporter, cscK encodes a fructokinase, and cscR encodes a repressor.

A third mechanism for utilizing sucrose, which is also PTS-independent, might in some cases use some of the same genes or type of genes as one of the other system. In this mechanism, invertase (for example that encoded by cscA) is released into the medium, either deliberately or by cell lysis, where it cleaves sucrose into glucose and fructose. The two monosaccharides are then imported into the cell and phosphorylated by the normal routes for those monosaccharides. This type of system is used by the yeast $Saccharomyces\ cerevisiae$, in which the invertase is encoded by a gene, for example SUC2, and the invertase is secreted to the periplasm and extracellular space. The resulting glucose plus fructose are then imported by facilitated duffusers, and the sugars are then kinased inside the cell.

A fourth mechanism for sucrose utilization, which is also PTS-independent, might also in some cases use some of the same genes or type of genes as one of the other systems. In this mechanism, sucrose is imported by, for example, a permease encoded by cscB, after which it s cleaved by phosphorolysis catalyzed by a sucrose phosphorylase. The resulting cytoplasmic glucose-1-phosphate and fructose are then metabolized by the normal routes for those metabolites.

One literature report (Alaeddinoglu and Charles 1979) states that the chromosomally encoded sucrose utilization genes of $E.\ coli$ that are integrated near the dsdA locus (presumably cscRAKB) require an intact ptsI gene in order to function. This statement contradicts the bulk of the rest of the literature, which states that the cscRAKB genes encode a PTS-independent system. Given this apparent contradiction, it is possible that the one of the systems that we have defined as the "PTS-independent" system might in fact have some dependence on the PTS system.

In one aspect, the present invention discloses the addition of genes to an organism in order to install or increase the activity of one or more proteins and/or enzymes involved in the import and conversion of sucrose into metabolic intermediates such as fructose 1,6-bisphosphate that can be further metabolized by the cell. The genes that encode relevant proteins or enzymes (herein called a "sucrose utilization function") suitable for genetic manipulation of this invention are selected from a list consisting of genes that encode a PTS-dependent sucrose importer (a PTS protein usually named Enzyme $II^{scr}$, or $EII^{scr}$ that functions together with other PTS proteins to accomplish the import and phosphorylation of sucrose to give cytoplasmic sucrose-6-hophate), sucrose-6-phosphate hydrolase, fructokinase, sucrose permease (a PTS-independent permease that transports sucrose into the cell without concomitant phosphorylation), invertase or sucrose hydrolase, sucrose phosphorylase, glucose kinase (also known as glucokinase), fructose kinase (also known as fructokinase), hexose-phosphate isomerase, and phosphofructo kinase (fructose-1-phosphate kinase).

In another embodiment, the present invention provides a process for producing succinic acid or other chemicals using sucrose as a renewable feedstock. In one aspect, the present invention provides a process for producing succinic acid from a sucrose-containing medium that makes use of a biocatalyst that has a decreased activity in at least one protein of the organism's native PTS system relative to that of the ancestral or parental strain. In another aspect, the present invention provides a process for producing succinic acid or other chemical in a sucrose containing medium which makes use of a biocatalyst which has retained a fully functional native PTS-dependent system for sugar uptake.

The PTS was originally discovered in E. coli and it is now known to play an important role in carbohydrate transport in a vast number of bacterial species. The molecular organization of PTS is very well understood. Across bacterial species, PTS is highly conserved in its basic organization. The present invention provides biocatalysts wherein the components of PTS are genetically transferred from a second donor bacterium to a first recipient bacterium in order to enable the biocatalyst to better use a desirable carbohydrate source in fermentation. In particular, the present invention provides biocatalysts that can utilize sucrose-containing renewable feedstock in the fermentative production of products such as succinic acid. More specifically, the present invention provides biocatalysts that can utilize sucrose and molasses derived from sugarcane processing in the production of succinic acid through biological fermentation. Since the trisaccharide raffinose contains sucrose, all aspects of this invention that apply to sucrose will also apply to raffinose, as long as a raffinose cleaving system is present in the biocatalysts.

The basic composition of PTS is similar in all bacterial species studied so far. It contains three major components namely EI, HPr, and EII. EI and HPr components are in the cytoplasm and are known as "general" components as they can work in conjunction with variety of carbohydrate-specific EII components.

The EII component contains three sub-components namely EIIA, EIIB and EIIC. The EIIB and EIIC proteins are membrane bound and EIIA component is located in the cytoplasm or the cytoplasmic side of a membrane protein. The enzyme EII either can form a single protein with three domains (A, B, and C) or can be split into two to four distinct proteins. EII is carbohydrate specific and E. coli is reported to have at least 15 different EII complexes. Thus the EII component specific for the glucose transport across the membrane is designated as $EIIA^{Glc}/EIICB^{Glc}$.

All the components of the PTS are proteins in nature. The genes coding for the various components of PTS have been identified. The ptsI gene in E. coli codes for the 63 kDa EI protein. The 10 kDa histidine containing phosphocarrier protein HPr is coded by the ptsH gene in E. coli. $EIIA^{Glc}$ protein is coded by the crr (carbohydrate resistance repression resistant) gene. $EIICBG^{Glc}$ protein is encoded by the ptsG gene in E. coli.

The PTS system is not only responsible for the transport of various carbohydrates across the cell membrane but also catalyzes the conversion of carbohydrates into their respective phosphoesters during the transport. The coupled transport and phosphorylation of carbohydrates by PTS is achieved by the interaction among EI, HPr, and EII protein components.

During glycolysis, four moles of PEP are produced from two moles of glucose, and half of the PEP is consumed to provide energy for glucose uptake. In the case of sucrose import, of two moles of hexose arising from one mole of sucrose also produce four moles of PEP, but only one mole of PEP is consumed for the sucrose transport, thus increasing 1.5 times the amount of PEP available as a source of carbon skeletons for biosynthesis within the cell when sucrose is used as the source of carbon. It is possible to further improve the yield of succinic acid and other chemicals by providing the E. coli with a PTS-independent sucrose utilization system which does not consume PEP for the import of sucrose. This approach is particularly advantageous for production of chemicals that are derived at least in part from or through PEP, such as succinate, malate, fumarate, lactate, ethanol, butanols, propane diols, 3-hydroxypropionic acid, acrylic acid, propionic acid, lactic acid, amino acids such as glutamate, aspartate, methionine, lysine, threonine, and isoleucine, and many other compounds.

The present invention provides ways to manipulate a PTS and in turn the bacterial carbohydrate utilization pattern. Since EI and HPr proteins protein function as "general component" of the PTS system, inactivation of either the ptsI gene coding for EI protein or the ptsH gene coding for HPr protein would lead to the complete inactivation of PTS. There will be substantially less carbohydrate transport through the PTS system in bacterial cells where the activity of ptsH or ptsI has been decreased. When the PTS is partially or completely inactivated, the bacterial cell has to depend on one or other alternative permease systems for carbohydrate transport. On the other hand, when the gene coding for a carbohydrate-specific particular EII component is inactivated, only the transport of that particular carbohydrate dependent on the inactivated EII component would be blocked. Thus the inactivation of crr or ptsG genes would block only the transport of the glucose through PTS, and the transport of other carbohydrates would occur normally.

When there is active glucose transport through PTS, the $EII^{Glc}$ remains unphosphorylated as there is a carbohydrate substrate for accepting its phosphate group. However, when there is no glucose in the medium, the phosphorylated form of $EII^{Glc}$ cannot transfer its phosphate group to glucose and therefore it remains in its phosphorylated state. The unphosphorylated $EII^{Glc}$ mediates the phenomenon generally known as carbon catabolite repression (CCR). Under CCR, when glucose is present in the growth medium, the transport and utilization of other carbohydrates in the medium is prevented until the glucose in the medium is completely utilized. The carbon catabolite repression results from the inhibitory effect of unphosphorylated $EII^{Glc}$ on the permease systems. A number of permeases involved in the carbohydrate transport are known to be inhibited by unphosphorylated $EII^{Glc}$. In addition, the unphosphorylated $EII^{Glc}$ is known to have a negative effect on the transcription of number of genes involved in carbohydrate transport and metabolism through its influence on the adenylate cyclase system. Thus, under certain circumstances, it is advantageous to decrease activity of the glucose-specific PTS system in order to relieve the cell from carbon catabolite repression.

In the fermentative production of succinic acid, there is a need to conserve PEP within the cell. PEP can act as the substrate for carboxylating enzymes within the cell. Carboxylation of the PEP yields oxaloacetic acid which enters into the tricarboxylic acid cycle and contributes to succinic acid production. The importance of the carboxylation of PEP in the biological production of succinic acid is very well recognized as evidence by the fact that some of the more successful biocatalysts currently in use for succinic acid production, such as KJ122, have a PTS that is at least partially reduced in activity and carbohydrate transport is at least partially mediated by a PTS-independent permease system. Reduction of PTS activity helps in conserving PEP. In addition, biocatalysts for succinic acid production such as KJ122 have genetic modifications leading to an increase in the rate of carboxylation of PEP (Zhang et al., 2009 a, b). Thus in the KJ122 strain developed for succinic acid production, the PTS is at least partially inactivated by a mutation in the ptsI gene. In addition, the PEP carboxykinase gene pck has acquired a mutation causing an increase in the specific activity for carboxylation of PEP. While it is advantageous to reduce the activity of the PTS when glucose is used as the source of inorganic carbon in the fermentative production of succinic acid, the same strategy might not be optimal for developing a strain for succinic acid production using sucrose as the primary source of organic carbon.

In one embodiment, the present invention provides a process for reactivating the "general Component" of the PTS system in the KJ122 strain and at the same time inactivating the glucose uptake through the PTS system. The mutated ptsI gene in KJ122 is replaced by a wild type ptsI gene and ptsG gene is deleted. These genetic manipulations allow the transport of carbohydrates other than glucose through PTS. Further, the elimination of the ptsG gene eliminates the carbon catabolite repression resulting from the unphosphorylated EIIA$^{Glc}$ protein. This situation is in contrast to the situation when the ptsI gene is mutated. In the bacterial cell with an intact ptsI gene and deletion of ptsG, the EIIA$^{Glc}$ protein is expected to be in its phosphorylated state. When the EIIA$^{Glc}$ protein is in its phosphorylated state, it does not cause any inhibitory acts on other permeases and on the transcription of the genes involved in carbohydrate metabolism.

When sucrose is transported through a PTS, it enters into the cell in the phosphorylated form as sucrose-6-phosphate. Further metabolism of sucrose-6-phosphate within the cell involves the following biochemical reactions. In the first step, sucrose-6-phosphate is hydrolysed through an appropriate hydrolyzing enzyme such as sucrose-6-phosphate hydrolase to release glucose-6-phosphate and fructose. The glucose-6-phosphate is converted into fructose-6-phosphate by the action of isomerase enzyme. In the next steps, fructose-6-phosphate is further phosphorylated to form fructose 1-6 bisphosphate which is in turn cleaved into phosphoglyceraldehyde and dihydroxyacetone phosphate. Both these three carbon compounds derived from fructose-1,6-bisphosphate will enter into the tricarboxylic acid cycle and provide the carbon backbone for succinic acid production.

The fructose released from the hydrolysis of sucrose-6-phosphate needs to be phosphorylated before it can enter the glycolytic pathway. The phosphorylation of fructose is mediated by fructokinase. When there is no endogenous fructokinase or when the activity of endogenous enzyme is low, it is necessary to provide an additional source of fructokinase enzyme activity by means of introducing an exogenous gene coding for the fructose kinase enzyme activity.

This approach of inactivating the ptsG gene and transporting sucrose through PTS is possible only in those strains where there is a sucrose-specific EIIA/CB component of the PTS. This protein is called among other names Enzyme II$^{scr}$. When there is no such endogenous sucrose-specific EIIA/CB component in the strain already developed for succinic acid production, there is a need to provide exogenous genes coding for sucrose-specific EIIA/CB components, which can function together with the "general components" of PTS already present in the biocatalyst for succinic acid production.

In another embodiment of the present invention, where there is a need to maintain the PTS in a state of reduced activity for the purpose of maintaining a sufficient pool of PEP as the substrate for carboxylase and/or carboxykinase enzyme, the sucrose transport can be facilitated by using a PTS-independent sucrose permease. Under the circumstance where the biocatalyst already developed for succinic acid production does not have a gene coding for non-PTS sucrose specific permease, it is necessary to introduce an exogenous gene that could mediate non-PTS sucrose transport into the cell. A number of bacterial strains such as *E. coli* W strain are reported to have an operon coding for proteins involved in the non-PTS sucrose transport into the cell. Any one of those known sucrose permease operons from other bacterial strains can be introduced into those bacterial strains lacking capacity for non-PTS of sucrose transport. An example of this non-PTS sucrose uptake is encoded by the chromosomal cscRAKB genes present near the dsdA (D-serine deaminase) locus in some, but not all, strains of *E. coli*. Examples of *E. coli* strains that contain the cscRAKB genes are EC3132 strain of *E. coli* and ATCC 9637 strain of *E. coli*, also known as *E. coli* W or the Waksman strain, *Klebsiella pneumoniae*, *Salmonella* ssp., *Erwinia amylovora* and many others.

Certain strains of *E. coli* such as the W strain of *E. coli* (ATCC 9637) are known to possess a chromosomally encoded PTS-independent sucrose-transport and metabolic pathway. Three different genes involved in the PTS-independent sucrose transport and metabolism, namely cscB, cscA, and cscK are organized in the chromosomal DNA as an operon. The cscB gene codes for a sucrose:H+ symporter. The cscA gene codes for an invertase enzyme which cleaves the sucrose transported into the cell into glucose and fructose. The cscK gene codes for a fructokinase. The csc operon is under the control of a repressor protein coded by the cscR gene. In one specific embodiment of the present invention, the cscA, cscB and cscK genes were introduced into a succinate production strain KJ122, without an intact regulatory control gene cscR. These three genes, cscABK, can be introduced into KJ122 strain on a self-replicating plasmid or, preferably, can be integrated into the host chromosome. In a preferred embodiment, the three genes, cscABK, are integrated at a non-essential region of the host chromosome (a region where insertion of the added genes do not have a significantly negative influence on any relevant aspect of growth or production of the desired product such as succinate in a commercial process) and the added genes are expressed from one or more appropriate constitutive promoters.

The titer of product from sucrose is equal to at least the titer produced by the parent organism from glucose, and the yield of product is greater than 0.8 gram of succinic acid produced/gram of sucrose consumed. The exogenous genes introduced into the cell can be maintained within the cell on a self-replicating plasmid. A plasmid can be maintained through antibiotic selection or complementation of a chromosomal mutation. Preferentially, the exogenous genes are integrated into the host chromosome so that there is no need to add any antibiotics to maintain the plasmids within the cell. There are several possible locations within the cell for the integration of the exogenous genes. The preferential locations for integrating the exogenous genes within the *E. coli* chromosomal DNA includes regions with no essential functions for growth and product formation under commercial fermentation conditions.

These PTS-independent sugar permeases facilitate sucrose transport into the cell without any chemical modifications. The PTS-independent sucrose permease system include solute-cation symport systems, such as the ScrT symporter in the sucrose operon in *Bifidobacterium lactis* and the CscB transporter of *E. coli*. These sucrose-specific transport systems are generally clustered with the catabolic and regulatory genes in various arrangements in different bacteria.

When the exogenous genes are obtained as an operon, it is preferential to remove any possible negative regulatory genes or proteins from the operon. It is ideal to have only the genes and proteins that function positively in sucrose transport and metabolism. Thus, expression of sucrose utitilisation genes is preferably not inhibited by a repressor or by carbon catabolite repression.

When a non-PTS sucrose transport system is used as the transport mechanism, the sucrose entering into the cell is still in an unphosphorylated form and it is necessary to phosphorylate the sucrose before it can enter into the metabolic pathway within the cell. Sucrose can be phosphorylated using an endogenous sucrose kinase already present within the cell. In the event that there is no endogenous sucrose kinase within the cell, exogenous DNA coding for sucrose kinase can be introduced into the cell. Once the sucrose is phosphorylated, the resulting sucrose-6-phosphate can be metabolized by the actions of the enzymes sucrose-6-phosphate hydrolase, glucose-6-phosphate isomerase, fructokinase, phosphofructokinase and fructose 1,6-bisphosphate aldolase as described above. Again, if necessary, genes encoding these enzymes can be introduced into the biocatalyst being developed. As an alternative, after sucrose enters the cell, it can be cleaved into glucose and fructose by an invertase. The resulting glucose and fructose can enter into metabolism by actions of the enzymes glucokinase and fructokinase respectively.

Phosphorylation of sucrose can also be accomplished by (sucrose phosphorylase (SPase). Sucrose phosphorylase catalyses conversion of sucrose (α-D-glucopyranosyl-1,2-β-D-fructofuranoside) and phosphate into D-fructose and α-G-1-P (α-D-glucose 1-phosphate). This phosphorolysis reaction accomplishes two steps required for the carbons of sucrose to enter into central metabolism, 1) the cleavage of the disaccharide into two monosaccharides, and 2) the phosphorylation of at least one of the monosaccharides. Another benefit of this phosphorolysis is that it does not consume an ATP for the phosphorylation as does the glucokinase reaction. Instead the energy for formation of the phosphate bond is derived from the energy released by hydrolysis. As such, an improvement in the efficiency of sucrose utilization can be realized by introducing, for example besides the cscAKB genes of E. coli W strain, a gene encoding a sucrose phosphorylase into a bacterial cell with no ability for sucrose utilization. Alternatively, the invertase gene, cscA can be replaced with a gene encoding sucrose phosphorylase. Several sucrose phosphorylases have been described (Goedl et al., 2007). Any such gene encoding a sucrose phosphorylase can be cloned and expressed in a recipient strain by methods well known in the art. In a preferred embodiment, an expression cassette that includes a sucrose phosphorylase gene is integrated into the chromosome of a recipient strain.

The PTS-dependent and the PTS-independent permease systems for sucrose transport are not mutually exclusive of each other. It is possible to have a functionally active PTS along with a functionally active PTS-independent permease system for sucrose transport within a single bacterial cell.

According to the present invention, it is disclosed to genetically transfer one or more sucrose transport and utilization systems from one or more donor organisms that naturally contain the relevant genes (for example scrKYABR, cscRAKB, scrP, spl, or a combination, or a subset thereof) into a recipient organism that does not naturally contain said relevant genes, so as to confer on said recipient organism a new ability to utilize sucrose or to enhance an already existing sucrose utilization capacity. ScrP and Spl are genes that encode a sucrose phosphorylase. Examples of said recipient organisms that do not naturally contain relevant sucrose transport and utilization genes include, but are not limited to, *E. coli* K-12 strains (such as EMG2, MG1655, W3110, W3350, C600, and DH5α), which is the strain background for the vast majority of genetic engineering work done in *E. coli*, ATCC 8739 (*E. coli* C), ATCC 11303 (*E. coli* B), BL21 (see New England Biolabs catalog, 2007-2008) and derivatives of these strains, Other examples of said recipient organisms includes a wide variety of other bacteria and archea that do not have a native ability to utilize sucrose, or that utilize sucrose poorly. The only limitation is that the recipient organism must be capable of being genetically altered (by genetic engineering, mating, transduction, transformation, etc.), such that the sucrose utilization genes of the invention may be installed in the recipient strain. The recipient organism can also be of a type that has already been constructed, selected, screened, bred, or otherwise altered such that it can already produce a chemical of interest. An example of this type of recipient strain is KJ122 (Jantama et al., 2008 a, b) and an example of a chemical of interest is succinic acid.

Other examples of recipient organisms include, but are not limited to: *Gluconobacter oxydans, Gluconobacter asaii, Achromobacter delmarvae, Achromobacter viscosus, Achromobacter lacticum, Agrobacterium tumefaciens, Agrobacterium radiobacter, Alcaligenes faecalis, Arthrobacter citreus, Arthrobacter tumescens, Arthrobacter paraffineus, Arthrobacter hydrocarboglutamicus, Arthrobacter oxydans, Aureobacterium saperdae, Azotobacter indicus, Brevibacterium ammoniagenes, divaricatum, Brevibacterium lactofermentum, Brevibacterium flavum, Brevibacterium globosum, Brevibacterium fuscum, Brevibacterium ketoglutamicum, Brevibacterium helcolum, Brevibacterium pusillum, Brevibacterium testaceum, Brevibacterium roseum, Brevibacterium immariophilium, Brevibacterium linens, Brevibacterium protopharmiae, Corynebacterium acetophilum, Corynebacterium glutamicum, Corynebacterium callunae, Corynebacterium acetoacidophilum, Corynebacterium acetoglutamicum, Enterobacter aerogenes, Erwinia amylovora, Erwinia carotovora, Erwinia herbicola, Erwinia chrysanthemi, Flavobacterium peregrinum, Flavobacterium fucatum, Flavobacterium aurantinum, Flavobacterium rhenanum, Flavobacterium sewanense, Flavobacterium breve, Flavobacterium meningosepticum, Micrococcus* sp. CCM825, *Morganella morganii, Nocardia opaca, Nocardia rugosa, Planococcus eucinatus, Proteus rettgeri, Propionibacterium shermanii, Pseudomonas synxantha, Pseudomonas azotoformans, Pseudomonas fluorescens, Pseudomonas ovalis, Pseudomonas stutzeri, Pseudomonas acidovolans, Pseudomonas mucidolens, Pseudomonas testosteroni, Pseudomonas aeruginosa, Rhodococcus erythropolis, Rhodococcus rhodochrous, Rhodococcus* sp. ATCC 15592, *Rhodococcus* sp. ATCC 19070, *Sporosarcina ureae, Staphylococcus aureus, Vibrio metschnikovii, Vibrio tyrogenes, Actinomadura madurae, Actinomyces violaceochromogenes, Kitasatosporia parulosa, Streptomyces coelicolor, Streptomyces flavelus, Streptomyces griseolus, Streptomyces lividans, Streptomyces olivaceus, Streptomyces tanashiensis, Streptomyces virginiae, Streptomyces antibioticus, Streptomyces cacaoi, Streptomyces lavendulae, Streptomyces viridochromogenes, Aeromonas salmonicida, Bacillus pumilus, Bacillus circulans, Bacillus thiaminolyticus, Escherichia freundii, Microbacterium ammoniaphilum, Serratia marcescens, Salmonella typhimurium, Salmonella schottmulleri, Bacillus subtilis, Bacillus licheniformis, Bacillus amylolliquefaciens* and *Xanthomonas citri*.

The present invention will be explained in detail below. The bacterium belonging to the genus *Escherichia* of the present invention is a strain which is constructed from a sucrose non-assimilative *Escherichia coli* as a parental strain, and which after construction harbors sucrose genes, preferably sucrose PTS-independent genes and has the ability to produce succinic acid.

The genetic materials for conferring sucrose utilization capacity to a recipient bacterial strain can be obtained from a number of donor bacterial strains. Depending on the donor bacterial strain serving as the source of genetic material for conferring sucrose utilization capacity, the recipient strain acquires either the PTS-dependent sucrose utilization capacity or a PTS-independent sucrose utilization capacity.

*Clostridium acetobutyllicum* ATCC 824 and *Clostridium beijerinickii* are known to transport sucrose through a PTS. The operon for sucrose transport and metabolism in each of these organisms is reported to code for three functional proteins and one regulatory protein. Thus in *Clostridium acetobutylicum*, the sucrose transport and metabolism operon contains the genes scrA, scrB, scrK and scrT encoding Enzyme II of the PTS, sucrose-6-phosphate hydrolase, fructokinase, and an antiterminator regulatory protein, respectively. In the case of *Clostridium beijerinickii*, the sucrose transport metabolism operon contains the genes scrA, scrB, scrK and scrR encoding Enzyme II of the PTS, sucrose-6-phosphate hydrolase, fructokinase, and a regulatory protein, respectively. When it is required to convert a bacterial strain incapable of utilizing sucrose into a sucrose-utilizing strain, only the scrA, scrB and scrK genes obtained from either one of the *Clostridial* species are introduced into sucrose-PTS negative strain. All these three genes can be derived from a single *Clostridium* species. Alternately, one or two genes may be derived from one species and the rest of the genes may be derived from another species.

*Staphylococcus xylosus* can be a source for a scrA gene coding for a sucrose specific PTS protein and a scrB gene coding for sucrose phosphate hydrolase.

*Mannheimia succiniproducens* is another source for a gene coding for sucrose specific PTS protein. The gene MS0784 of *M. succiniproducens* has recently been shown to code for a protein with sucrose specific PTS function. The gene MS0909 has recently been shown to code for a protein with sucrose 6-phosphate hydrolase activity. *Corynebacterium glutamicum* is yet another source of genes useful in the present invention. Sucrose PTS gene encoding for sucrose EIIBCA protein as well as that sucrose-6-phosphate hydrolase can be obtained from the sucrose PTS operon of *C. glutamicum*. The fructose PTS operon of *C. glutamicum* can be used as the source of a fructose-1-phosphate kinase gene. Both *Corynebacterium glutamicum* and *Mannheimia succiniproducens* lack the fructokinase gene and the fructose released from the hydrolysis of sucrose-6-phosphate is released into the medium and taken up through a fructose PTS. One way to improve the sucrose utilization in those strains lacking fructose kinase enzyme activity is to introduce an exogenous gene coding for fructose kinase enzyme.

Other sources of sucrose utilization genes and proteins are as follows: The sucrose-specific PTS protein ScrA can be derived from *Erwinia chrysanthemi* 3937. Similarly *Bacillus subtilis* can be source for sucrose-specific PTS protein SacP. *B. subtilis* sacP gene codes for EIIBC$^{scr}$ protein presumably functioning with EIIA$^{glu}$ to transport sucrose. The sacA gene codes for sucrose-6-phosphate hydrolase which hydrolyzes the intracellular sucrose-6-phosphate.

In the scrARBK operon of *Clostridium* species, scrA codes for EIIBC$^{scr}$ domain of the sucrose PTS, which is probably complemented by the EIIA$^{glu}$ protein. scrB codes for sucrose hydrolase and scrK codes for fructokinase. In the *Staphylococcus xylosus*, scrA is separate from scrB and scrK. The scrA gene codes for EIIBC$^{scr}$. The scrB gene codes for sucrose hydrolase and scrK codes for fructokinase. In the gram-positive lactic acid bacteria *Pediococcus pentosaceus, Lactobacillus plantarum*, and *Streptococcus mutans* scrA codes for a sucrose PTS protein. scrB codes for sucrose-6-P hydrolase. scrK codes for fructokinase. In the enteric bacteria *Salmonella* spp the conjugative plasmid and conjugative transposon have a scrKYABR operon. scrK codes for fructokinase, scrY codes for an outer membrane porin, scrA codes for EII$^{scr}$ transport protein, and scrB codes for a sucrose-6-p hydrolase. *Erwinia amylovora* has the same gene cluster scrKYABR as in *Klebsiella pneumonia* and pUR400. *Vibrio alginolyticus* has the scrRAKB operon. The scrA gene encodes an EIIBC$^{scr}$ protein that is complemented by the *E. coli* EIIA$^{glu}$ subunit and scrB codes for sucrose hydrolase.

*E. coli* wild type isolate EC3132 can use sucrose while the *E. coli* strain K12 can not utilize sucrose. The non-PTS genes involved in the sucrose utilization and metabolism namely cscB, cscK, cscA and cscR are chromosomally situated in EC3132. These cscB, cscK, cscA and cscR genes from *E. coli* strain EC3132 can be introduced into the *E. coli* strain K12 to confer sucrose utilization capacity to K12 *E. coli* strain.

The sucrose phosphorylase gene can be obtained from *Bifidobacterium longum, Leuconostoc mesenteroides* (for example strain DSM 20193), *Pseudobutyrivibrio ruminis*, or *Bifidobacterium lactis* DNA. The scrP gene of *B. lactis* and spl gene of *B. longum* code for sucrose phosphorylase.

*B. longum* can be a source for permease, phosphorylase and fructokinase genes. In *B. longum*, the permease (scrT) and phosphorylase (scrP) genes occur in a operon along with a gene coding for a transcriptional regulator (scrR). Also present in *B. longum* is a fructokinase gene (frk) which is induceable by fructose and is subjected to glucose-mediated repression. By means of using specific primer sets, the open reading frames of these genes can be obtained and expressed in the biocatalyst using appropriate promoters.

Genes coding for glucokinase and fructokinase can be obtained from *Zymomonas mobilis*. A glucokinase with broad hexose specificity can be obtained from *Bacillus sphaericus* C3-41. The glucokinase from this bacterial species has been shown to phosphorylate fructose and mannose as well. Genomic *E. coli* glk-encoded glucokinase alone or in combination with plasmid-localized *Zymomonas mobilis* glk-encoded glucokinase also catalyzes the phosphorylation of glucose. Besides the copy of the glk already present in the genomic DNA of *E. coli*, additional copies of the glk gene is provided on a of low copy plasmid under the control of certain constitutive promoters, or integrated into the chromosome.

The exogenous genes introduced into the cell can be maintained within the cell on a self-replicating plasmid. A plasmid can be maintained through antibiotic selection or complementation of a chromosomal mutation. However, when the exogenous genes are maintained within the biocatalyst on a self-replicating plasmid within the cell, it is necessary to assure the there is no unnecessary waste of energy and materials leading to the inhibition of growth, and a decrease in the yield or productivity of the organic material being manufactured using the biocatalyst. Preferentially, the exogenous genes are integrated into the host chromosome so that there is no need to add any antibiotics to maintain the plasmids within the cell. There are several possible locations within the cell for the integration of the exogenous genes. The preferential locations for integrating the exogenous genes within the E. coli chromosomal DNA includes regions with no essential functions for growth and product formation under commercial fermentation conditions.

When the exogenous genes are obtained as an operon, it is preferable to remove any possible negative regulatory genes or proteins from the operon. It is ideal to have only the genes and proteins that function positively in sucrose transport and metabolism. Thus, expression of sucrose utilization genes is preferably not inhibited by a repressor or by carbon catabolite repression.

The genes necessary for sucrose utilization can be derived from two separate donor organisms. For example, the scrK gene for fructokinase could be derived from K. pneuomoniae, and the cscsA and cscB genes could be derived form E. coli W strain, and the three genes could be combined into one recipient strain. As another example, a gene encoding sucrose phosphorylase from Leuconostoc meseteroides could be installed together with the cscB and cscK genes from E. coli W strain, either with or without the cscA gene.

Any bacterium which is sucrose non-assimilative and has the capacity to produce succinic acid can be improved according to the present invention.

The bacterium of the present invention may be obtained by introduction of genes that utilize sucrose by a PTS-dependent sucrose utilizing system or a PTS-independent sucrose utilizing system into a succinic acid producing strain such as KJ122. Alternatively the bacterium of the present invention may be obtained by conferring an ability to produce succinic acid to a bacterium in which a PTS-dependent sucrose utilizing system or a PTS-independent sucrose utilizing system is already present. This latter alternative can be accomplished, for example, by following all the steps used for constructing KJ122 (disclosed in Janatama et al., 2008), but starting with strain ATCC 9637 instead of starting with strain ATCC 8739.

The source of a PTS-dependent sucrose utilizing system or a PTS-independent sucrose utilizing system is not particularly limited as long as the relevant genes can function or be made to function in the bacterial cell of interest.

The following examples are provided as a way of illustrating the present invention and not as a limitation.

EXAMPLE 1

Construction of SD14, a Derivative of KJ122 that Contains the cscBKA Gene Cluster from E. Coli W The cscBKA gene cluster encoding genes for sucrose utilization uptake and utilization, was amplified from the genomic DNA of the W strain of Escherichia coli (ATCC 9637) using polymerase chain reaction. The PCR primers were designed in such a way so that the resulting PCR product contained only the cscB, cscK, and cscA genes from the original csc operon in the W strain and not a functional cscR gene encoding for a repressor protein. In addition to sequences homologous to the csc operon, the primers for PCR amplification included at the 5' end 50 bases (bp) of sequences that are homologous to the site for integration into the E. coli KJ122 chromosome. The sequences of the PCR primers used in this example are listed in the Table 1. The target site for integration is 291 bp upstream from the rrnC gene. This site does not code for any known genes thus minimizing the possibility of disrupting an important E. coli genetic function.

The PCR product obtained by using primers SD032 and SD033 and ATCC 9673 chromosomal DNA as template was purified using Qiagen QIAquick PCR Purification Kits as instructed by the manufacturer. The purified fragments were then transformed into KJ122 containing pKD46 helper plasmid according to the method described by Datsenko and Wanner. (Datsenko and Warner 2000). pKD46 is available from the Coli Genetic Stock Center, Yale University, New Haven, Conn. Selection was for growth on minimal sucrose plates. The resulting strains were tested for correct integration of the csc genes at the intended target site upstream from rrnC by diagnostic PCR using primers SD033 through SD036 in various appropriate combinations. The correct strains grew well on minimal sucrose medium and gave red colonies on MacConkey sucrose plates. For all culture media, sucrose was ultrapure (for example Sigma catalog number S 7903). Sucrose stock solutions were made 50% (weight/volume) in deionized water and sterilized by filtration through disposable Nalgene 0.2 micron nylon membrane filter units. One particular isolate named SD14 was used for further work.

In a fashion similar to that described above, any DNA sequence that encodes sucrose utilization genes (either PTS-independent or PTS-dependent, for example, an scrKYBA operon from Klebsiella pneumoniae or pUR400) can be amplified by PCR and integrated into the chromosome of a recipient strain at the same target described above or at any suitable other target. For example, by using primers SD038 and SD039, the cscBAK operon of E. coli W can be integrated just upstream of the dnaA gene in KJ122.

FIGS. 1-5 provides the results of the experiments done with SD14 strain in a small scale microaerobic fermentors. FIG. 1 provides the data on the kinetics of sucrose utilization, and kinetics for the accumulation of glucose, fructose, and succinic acid. Also shown in FIG. 1 is the kinetics of bacterial growth. FIGS. 2-5 show the kinetics of sucrose utilization, kinetics of glucose accumulation, kinetics of fructose accumulation, and kinetics of succinic acid accumulation respectively. In the experiments described in the FIGS. 2-5, three different concentrations of sucrose (100 g/L. 150 g/L and 200 g/L) were used.

EXAMPLE 2

Analysis of Growth and Sucrose Utilization in the Recombinant Stain SD14 in a 7 Liter Fermentor The SD14 strain was grown in minimal medium supplemented with 10% sucrose. A stock solution containing both ammonium hydroxide and ammonium bicarbonate (7 N $NH_4OH$ and 3M $NH_4HCO_3$) was used to neutralize succinic acid produced in the fermentors at 39° C. The starting volume of 3 liters contained potassium phosphate monobasic (18 mM) magnesium sulfate (2 mM), betaine (1.33 mM), trace elements (Jantama et al., 2008a, b), Antifoam 204 (8 ppm) and sucrose batched at 98 g/l. pH was adjusted initially to pH 7.0 and thereafter was maintained at pH 6.5 by addition of the ammonium hydroxide/ammonium bicarbonate solution described above. Air was delivered at 5 ml/minute. The 150 ml inoculum was grown aerobically and contained a minimal medium with 2% sucrose and supplemented with 0.1 mM calcium chloride.

For comparison, KJ122 was fermented in the same medium with the same neutralization solution, except that the carbon source was glucose, which was batched at 25 g/l and then delivered in fed batch mode from a concentration of 220 g/l. Sugars, succinate, and byproducts were assayed by HPLC, as described (Zhang et al., 2009 a,b; Jantama et al., 2008 a, b).

Figure 6:
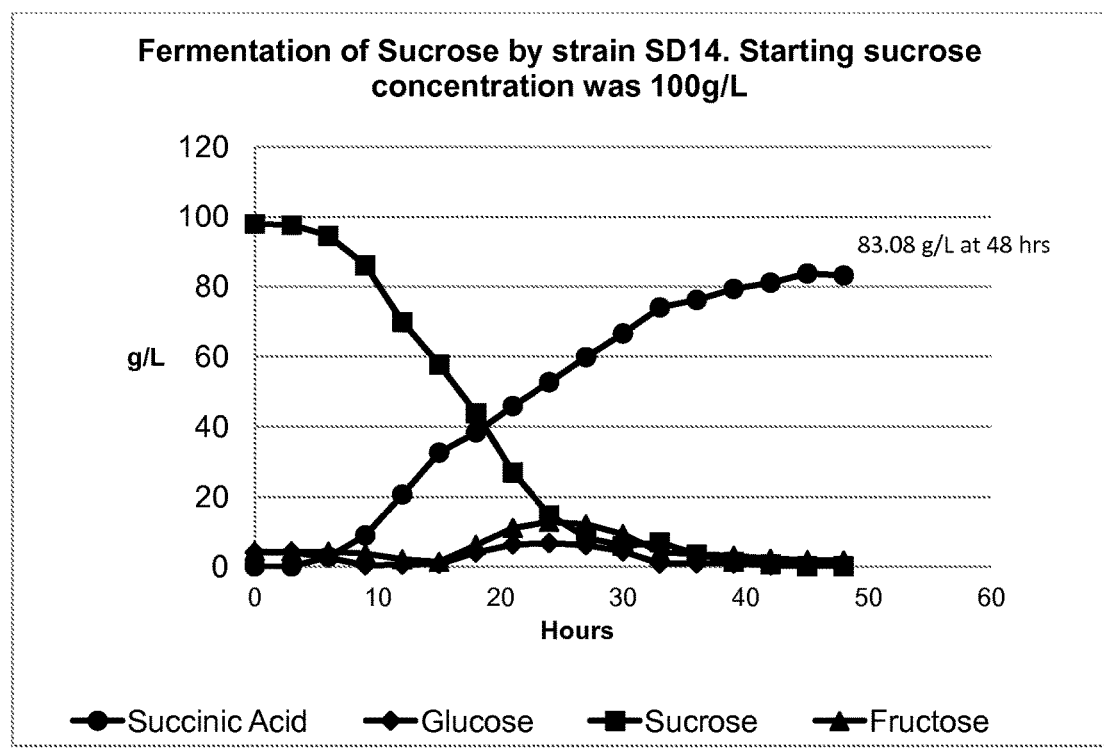
FIG. 6. Kinetics of succinic acid accumulation during fermentative growth of SD14 strain of *E. coli* in a 7,000 ml New Brunswick bioreactor with a starting volume of 3,000 ml and microaeration at the rate of 0.005 liter of air per minute.

The results are compared to a typical fed batch run of the parent strain KJ122 grown in glucose in Table 2. The kinetics of sucrose utilization, glucose accumulation, fructose accumulation and succinate production during the fermentation with SD14 is shown in FIG. 6. Sucrose was completely consumed by 50 hours and the succinic acid concentration in the medium reached a value of 83.08 grams per liter of fermentation broth at 50 hours. Glucose and fructose concentrations in the medium reached their peak around 25 hours.

EXAMPLE 3

Cloning and Expression of a Sucrose Phosphorylase in SD14

The sucrose phosphorylase gene from *Leuconostoc mesenteroides* strain DSM 20193 (Goedl et al., 2007) is cloned by PCR amplification using primers BY107 and BY108 (see Table 1) and genomic DNA as a template. The resulting 1594 bp PCR product is purified on a Quiagen QIAquick PCR purification column, cleaved with XbaI and BamHI restriction enzymes (New England Biolabs), and purified by agarose gel electrophoresis. The resulting fragment is ligated into the XbaI to BamHI backbone of pOM324 (US Patent Application 2009/0311756) to give plasmid pRY801, which places the sucrose phosphorylase gene under the control of a strong constitutive promoter. The promoter-sucrose phosphorylase gene-terminator cassette is excised from pRY801 by cutting with XhoI and BamHI, and the sticky ends of the resulting cassette are made blunt with the Quick Blunting Kit (New England Biolabs) and the blunted fragment is ligated into pMH17F (SEQ ID NO. 13) that had been cut with BsrBI and treated with calf intestine phosphatase (New England Biolabs), to give plasmid pRY802F (SEQ ID 14). In pRY802F, the sucrose phosphorylase expression cassette is flanked on each end with about 500 bp of DNA sequence that is homologous to a sequence just downstream of the thrV gene of strain SD14. The cassette and surrounding sequence is amplified by PCR using pRY802F as template and primers BY83 and BY84 (see Table 1). The resulting 2.7 kilobase fragment is purified on a Qiagen QIAquick PCR purification column. This fragment is then installed into SD14 next to the thrV locus by the two step gene replacement method of Jantama et al (2008 a, b), using a selectable and counterselectable cat-sacB cassette with the same flanking sequences homologous to the thrV region for the first step. For the first step, the cat-sacB cassette is obtained as a blunt Eco ICRI fragment from pCA2 and ligated into BsrBI cleaved, and calf intestine phosphatase treated, pMH17F as described above, to give plasmid pRY803F (SEQ ID NO 15). The cat-sacB cassette with surrounding sequences homologous to the thrV region is amplified by PCR using primers BY83 and BY84. The resulting 4 kb linear DNA product is used to transform SD14 to chloramphenicol resistance to give strain RY863. In the second step, the 2.7 kb linear DNA product described above (which contains the sucrose phosphorylase expression cassette from pRY802F) is used to transform RY863 to sucrose resistance (Jantama et al., 2008 a, b) to give strain RY864. The correct strain is verified using diagnostic PCR with chromosomal DNA as template and BY83 and BY84 as primers. The resulting strain, RY864, has the sucrose phosphorylase cassette integrated near thrV, and expresses a significant level of sucrose phosphorylase, which improves sucrose utilization efficiency by saving one ATP per mole of sucrose cleaved.

REFERENCES

U.S. Pat. No. 6,960,455
U.S. Pat. No. 7,179,623
US Patent Application Publication No. 20080275426
US Patent Application Publication No. 20090047719
US Patent Application Publication No. 20090253192
US Patent Application Publication No. 20090311756
US Patent Application Publication No. 20100184171
International Patent Application Publication No. WO2010/032698
International Patent Application Publication No. WO2010/053052
International Patent Application Publication No. WO2010/115067

Alaeddinoglu, N. G., and Charles, H. P. (1979) Transfer of a gene for sucrose utilization into *Escherichia coli* K12, and consequent failure of expression of genes for D-serine utilization, *J Gen Microbiol* 110, 47-59.

Bachmann, B. J. (1972) Pedigrees of some mutant strains of *Escherichia coli* K-12, *Bacteriol Rev* 36, 525-557.

Becker, J., Klopprogge, C., Zelder, O., Heinzle, E., and Wittmann, C. (2005) Amplified expression of fructose 1,6-Bisphosphatase in *Corynebacterium glutamicum* increases in vivo flux through the pentose phosphate pathway and lysine production on different carbon sources. Appl. Environ. Microbiol. 71: 8587-8596.

Bockmann, J., Heuel, H., and Lengeler, J. W. (1992) Characterization of a chromosomally encoded, non-PTS metabolic pathway for sucrose utilization in *Escherichia coli* EC3132, *Mol Gen Genet.* 235, 22-32.

Caescu, C., Vidal, O., Krzewinski, F., Artenie, V., and Bouquelet, S. (2004) *Bifidobacterium longum* requires a frucrokinase (Frk; ATP:D-fructose 6-phosphotransferase, EC 2.7.1.4) for fructose catabolism. J. Bacteriol. 186: 6515-6525.

Datsenko, K. A., and Wanner, B. L. (2000) One-step inactivation of chromosomal genes in *Escherichia coli* K-12 using PCR products, *Proc Natl Acad Sci USA* 97, 6640-6645.

Deutscher, J., Francke, C., and Postma, P W. (2006) How phosphotransferase system-related protein phosphorylation regulates carbohydrate metabolism in bacteria. Microbio. Mol. Bio. Rev. 70: 939-1031.

Doelle, H W. (1982) Kinetic characteristics and regulatory mechanisms of glucokinase and fructokinase from *Zymomonas mobilis*. European J. Appl. Microbiol. Biotechnol. 14: 241-246.

Dominquez, H., and Lindley, N D. (1996) complete sucrose metabolism requires fructose phosphotransferase activity in *Corynebacterium glutamicum* to ensure phosphorylation of liberated fructose. Appl. Environ. Microbiol. 62: 3878-3880.

Engels, V., Linden, S N., and Wendisch, V F. (2008) The global repressor SugR controls expression of genes of glycolysis and of the L-lactate dehydrogenase LdHA in *Corynebacterium glutamicum*. J. Bacteriol. 190: 8033-8044.

Goedl, C., Schwarz, A., Minani, A., and Nidetzky, B. (2007) Recombinant sucrose phosphorylase from *Leuconostoc mesenteroides*: characterization, kinetic studies of transglucosylation, and application of immobilised enzyme for production of alpha-D-glucose 1-phosphate, *J Biotechnol* 129, 77-86.

Han, B., Liu, H., Hu, X., Cai, Y., Zheng, D., Yuan, Z. (2007) Molecular characterization of a glucokinase with broad hexose specificity from *Bacillus sphaericus* strain C3-41. Appl. Environ. Microbiol. 73: 3581-3586.

Hernandez_Montalvo, V., Martinez, A., Hernandez-Chavez, G., Bolivar, F., Valle, F., Gosset, G. (2003) Expression of galp and glk in a *Eschericahi coli* PTS mutant restores glucose transport and increases glycolyitc flux to fermentation products. Biotechnol. Bioengineer. 83: 6897-694.

Hugouvieux-Cotte-Pattat, N., and Charaoui-Boukerzaza, S. (2009) Catabolism of raffinose, sucrose, and melibiose in *Erwinia* chrysanthemi 3937. J. Bacteriol. 191: 6960-6967.

Jahreis, K., Bentler, L., Bockmann, J., Hans, S., Meyer, A., Siepelmeyer, J., and Lengeler, J W. (2002) Adaptation of sucrose metabolism in the *Escherichia coli* wild type strain EC3132. J. Bacteriol. 184: 5307-5316.

Jankovic, I., and Bruckner, R. (2007) Carbon catabolite repression of sucrose utilization in *Staphylococcus xylosus*: Catabolite control protein CcpA ensures glucose preference and autoregulatory limitation of sucrose utilization. J. Mol. Microbiol. Biotechnol. 12: 114-120.

Jantama, K., Haupt, M J., Svoronos, S A., Zhang, X., Moore, J C. Shanmugam, K T., and Ingram, L O. (2008a) Combining metabolic engineering and metabolic evolution to develop nonrecombinant strains of *Escherichia coli* C that produce succinate and malate. Biotechnol. Bioeng. 99: 1140-1153.

Jantama, K., Zhang, X., Moore, J. C., Shanmugam, K. T., Svoronos, S. A., and Ingram, L. O. (2008b) Eliminating side products and increasing succinate yields in engineered strains of *Escherichia coli* C, Biotechnol. Bioeng. 101, 881-893.

Jiang, L., Cai, J., Wang, J., Liang, S., Xu, Z. and Yang, S T. (2010) Phosphoenolpyruvate-dependent phosphorylation of sucrose by *clostridium tyrobutyricum* ZJU 8235: evidence for the phosphotransferase transport system. Bioresour. Technol. 101: 304-9.

Lee, J., Mitchell, W J., Tangney, M., and Blaschek, H P (2005) Evidence for the presence of an alternative glucose transport system in *clostridium beijerinckii* NCIMB 8052 and the solvent-hyperproduciing mutant BA101. Appl. Environ. Microbiol. 71: 3384-3387.

Lee, J. W., Choi, S., Park, J. H., Vickers, C. E., Nielsen, L. K., and Lee, S. Y. (2010a) Development of sucrose-utilizing *Escherichia coli* K-12 strain by cloning beta-fructofuranosidases and its application for L-threonine production, *Appl Microbiol Biotechnol* 88, 905-913.

Lee, J W., Choi, S., Kim, J M., and Lee, S Y. (2010b) Mannheimia succiniproducens phosphotransferase system for sucrose utilization. 76: 1699-1703.

Moon, M-W., Kim, H-J., Oh, T-K., Shin, C-S., Lee, J-S., Kim, S-J., and Lee, J-K. (2005) Analyses of enzyme II gene mutants for sugar transport and heterologus expression of fructokinase gene in *Corynebacterium glutamicum* ATCC 13032. FEMS Mirobiol. Lett. 244: 259-266.

Neidhardt, F. C., and Curtiss, R. (1996) *Escherichia coli* and *Salmonella: cellular and molecular biology*, 2nd ed., ASM Press, Washington, D.C.

Reid, S J., and Abratt, V R. (2005) Sucrose utilization in bacteria: genetic organization and regulation. 67: 312-321.

Reizer, J., Bachem, S., Reizer, A., Arnaud, M., Saier Jr., M H., and Stulke, J. (1999) Novel phosphotransferase system genes revealed by genome analysis—the complete complements of PTS proteins encoded within the genome of *Bacillus subtilis*. Microbiology 145: 3419-3429.

Scholten, E., Renz, T, and Thomas, J. (2009) Continuous cultivation approach for fermentative succinic acid production from crude glycerol by *Basfia succiniciproducens* DD1. Biotechnol Lett 31:1947-1951.

Shukla, V B, Zhou, S., Yomano, L P., Shanmugam, K T, Preston, J F., Ingram, L O. (2004) Production of D(−)-lactate from sucrose and molasses. Biotechnol. Lett. 26: 689-693.

Tanaka, Y. Okai, N., Termoto, H., Inui, M., and Yukawa, H. (2008) Regulation of the expression of phosphoenolpyruvate: Carbohydrate phosphotransferase system (PTS) genes in *Corynebacterium glutamicum* R. Microbiol. 154: 264-274.

Tangney, M., Yazdanian, M., and Mitchell, W J. (1998) Sucrose transport and metabolism in *Clostridium beijerinckii*. J. Appl. Microbiol. 84: 914-9.

Tangney, M. and Mitchell W J (2002) Analysis of a catabolic operon for sucrose transport and metabolism in *Clostridium acetobutylicum* ATCC 824. J. Mol. Microbiol. Biotechnol. 2: 71-80.

Trindale, M I., Abratt, V R., and Reid, S J. (2003) Induction of sucrose utilization genes from *bifidobacterium lactis* by sucrose and raffinose. Appl. Environ. Microbiol. 69: 24-32.

Wang, J., Zhu, J., Bennett, G. N. and San, K-Y. (2011) Succinate production from different carbon sources under anaerobic conditions by metabolic engineered *Escherichia coli* strains. Metab. Eng. 13: 328-335.

Yi, J., Draths, K M., Li, K., and Frost J W. (2003) Altered glucose transport and shikimate pathway product yields in *E. coli*. Biotechnol. Prog. 19: 1450-1459.

Zhang, X. Jantama, K., Moore J C, Jarboe, L R., Shanmugam, K T., and Ingram, O. (2009a) Metabolic evolutiaon of energy-conserving pathway for succinate production of *Escherichia coli*. Proc. Natl. Acad. Sci. USA 106: 20180-20185.

Zhang, X., Jantama, K., Shanmugam, K. T., Ingram, L. O. (2009b) "Re-engineering *Escherichia coli* for succinate production in mineral salts medium." *App Environ Microbiol* 75: 7807-7813.

TABLE 1

Primers used in the PCR

| SEQ ID NO. | Primer No | Primer sequence (5' to '3) |
|---|---|---|
| SEQ ID NO. 1 | SD032 | taaatttcctcttgtcaggccggaataactccctataatgcgccaccact aggcgtttggattaggcgatt |
| SEQ ID NO. 2 | SD033 | ctcaggagaaccccgctgacccggcggcgtgtttgccgttgttccgtgtc gatccgttgttccacctgatatt |

TABLE 1 -continued

Primers used in the PCR

| SEQ ID NO. | Primer No | Primer sequence (5' to '3) |
|---|---|---|
| SEQ ID NO. 3 | SD034 | ttagtatgccaccaggaagt primes in rrnc flanking insert (has 1 mismatch with KJ122 sequence) |
| SEQ ID NO. 4 | SD035 | atgctcaaagaattaaactt primes in rrnc flanking insert (has 1 mismatch with KJ122 sequence) |
| SEQ ID NO. 5 | SD036 | cagttttcttcgcaatttcg primer internal to cscB |
| SEQ ID NO. 6 | SD037 | gacacgctcgccctaaggat primer internal to cscA |
| SEQ ID NO. 7 | SD038 | tggaaagtcctgtggataaatcgggaaaatctgtgagaaacagaagatct gagcgactgtaccagaacatga |
| SEQ ID NO. 8 | SD039 | agatcctgcaaaacgatcgggaccgcggatcatagcctaaactgcgcaag tcgccgtaatgggctttga |
| SEQ ID NO. 9 | BY83 | ttacctagagagggtgagaattgccgaacat |
| SEQ ID NO. 10 | BY84 | gatgagagaagattttcagcctgatacagatt |
| SEQ ID NO. 11 | BY107 | gggtctagaatagtggaggaataataatggaaattcaaaacaaag |
| SEQ ID NO. 12 | BY108 | cgcggatccttgtctgtcaatataatatttcccactatcagca |
| SEQ ID NO. 13 | pMH17F | plasmid clone of thrV region, spectinomycin resistance |
| SEQ ID NO. 14 | pRY802F | *Leuconostoc mesenteroides* strain DSM 20193 sucrose phosphorylase gene driven by a constitutive promoter, for integration at the thrV locus |
| SEQ ID NO. 15 | pRY803F | cat-sacB cassette for integration at thrV locus |

TABLE 2

Fermentation examples

| Strain | Carbon source | Succinate Titer g/l | Succinate Yield g/g | Fructose Titer g/l | Time |
|---|---|---|---|---|---|
| SD14 | Sucrose 98 g/l Batch | 83.1 | 0.85 | 1.80 | 45 hr |
| KJ122 | Glucose 106 g/l Fed batch | 82.6 | 0.86 | 0 | 48 hr |

What is claimed is:

1. A genetically altered *Escherichia coli* bacterium that produces at least 20 grams per liter of an organic chemical selected from the group consisting of succinic acid, fumaric acid, malic acid, and 1,4-butanediol, in a minimal medium, said bacterium comprising at least one exogenous gene that encodes a sucrose utilization function selected from the group consisting of a sucrose:H+ symporter, and a fructokinase.

2. The genetically altered *Escherichia coli* bacterium of claim 1, wherein said at least one exogenous gene that encodes a sucrose utilization function is contained in a replicating plasmid.

3. The genetically altered *Escherichia coli* bacterium of claim 1, wherein the bacterium is a phosphotransferase system+ bacterial strain.

4. The genetically altered *Escherichia coli* bacterium of claim 1, wherein the bacterium is a phosphotransferase system− bacterial strain.

5. The genetically altered *Escherichia coli* bacterium of claim 1, wherein said at least one exogenous gene that encodes a sucrose utilization function is integrated into the *Escherichia coli* bacterium chromosome.

6. A genetically altered *Escherichia coli* bacterium that produces at least 20 grams per liter of succinic acid in a minimal medium, said bacterium comprising at least one exogenous gene that encodes a sucrose utilization function selected from the group consisting of a sucrose:H+ symporter, and a fructokinase.

7. The genetically altered *Escherichia coli* bacterium of claim 6, wherein said at least one exogenous gene that encodes a sucrose utilization function is contained in a replicating plasmid.

8. The genetically altered *Escherichia coli* bacterium of claim 6, wherein said at least one exogenous gene that encodes a sucrose utilization function is integrated into the *Escherichia coli* bacterium chromosome.

9. The genetically altered *Escherichia coli* of claim 6, wherein said exogenous gene encodes an invertase enzyme with sucrose utilization function.

10. The genetically altered *Escherichia coli* bacterium of claim 6, wherein the bacterium is a phosphotransferase system$^+$ bacterial strain.

11. The genetically altered *Escherichia coli* of claim 6, wherein the bacterium is a phosphotransferase system$^-$ bacterial strain.

* * * * *